United States Patent [19]

Fournie-Zaluski et al.

[11] Patent Number: 5,591,891
[45] Date of Patent: Jan. 7, 1997

[54] N-[MERCAPTOACYL (AMINO ACID OR PEPTIDE )] COMPOUNDS AND S-LIPOPHILIC ALIPHATIC CARBONYL DERIVATIVES THEREOF AS ANTIHYPERTENSIVES

[75] Inventors: Marie-Claude Fournie-Zaluski, Paris; Bernard-Pierre Roques, Saint Maurice, both of France

[73] Assignee: Institut National de la Sante et de la Recherche Medicale (INSERM), Paris, France

[21] Appl. No.: 185,563

[22] Filed: Jan. 24, 1994

[51] Int. Cl.$^6$ .................................................. C07C 321/00
[52] U.S. Cl. .............................. 567/426; 546/249; 549/6; 549/491; 549/497; 549/504
[58] Field of Search .......................... 562/426; 549/491, 549/497, 504, 6; 546/249

[56] References Cited

U.S. PATENT DOCUMENTS

| | | | |
|---|---|---|---|
| 3,246,025 | 4/1966 | Mita et al. | 260/455 |
| 4,053,651 | 10/1977 | Ondetti et al. | 424/319 |
| 4,248,883 | 2/1981 | Sawayama et al. | 424/274 |
| 4,474,799 | 10/1984 | Greenberg et al. | 424/274 |
| 4,513,009 | 4/1985 | Roques et al. | 514/513 |
| 4,613,587 | 9/1986 | Kessler et al. | 514/19 |
| 4,684,660 | 8/1987 | Ondetti et al. | 514/423 |
| 4,738,803 | 4/1988 | Roques et al. | |
| 4,798,904 | 1/1989 | Delaney et al. | 558/254 |
| 4,879,309 | 11/1989 | Doll et al. | 514/513 |

FOREIGN PATENT DOCUMENTS

| | | |
|---|---|---|
| 0086757 | 8/1983 | European Pat. Off. |
| 0136883 | 4/1985 | European Pat. Off. |
| 2207351 | 2/1989 | United Kingdom. |

OTHER PUBLICATIONS

Roques et al., "The enkephalinase inhibitor thiorphan shows antinociceptive activity in mice", 1980, pp. 1–3, Nature, vol. 288, No. 5788.
Roques et al., "Complete differentiation between enkephalinase and angiotensin–converting enzyme inhibition by retro–thiorphan", 1983, Proc. Natl. Acad. Sci. vol. 80, pp. 3178–3182.
Roques et al., "Neutral endopeptidase-24. 11 ingibitors: from analgesics to antihypertensives?", Trends in Pharmacological Sciences, vol. 11, No. 6, 1990, pp. 245–249.
Fournie–Zaluski et al., "New Dual Inhibitors of Neutral Endopeptidase and Angiotensin–Converting Enzyme...", J. Med. Chem. 37, pp. 1070–1083, 1994.
J. G. C. Van Amsterdam et al., *European Journal of Pharmacology*, vol. 135, pp. 411–418 (1987).
T. Komori et al., *Chemical and Pharmaceutical Bulletin*, vol. 35(6), pp. 2388–2393 (1987).
F. Noble et al., *Journal of Pharmacol. Exp. Ther.*, vol. 261(1), pp. 181–190 (1992).
B. P. Roques et al., *Nature*, vol. 288, pp. 286–288 (1980).
J. A. Koehn et al., *J. Biol. Chem.*, vol. 262, pp. 11623–11627 (1987).
S. L. Stephenson et al., *Biochem. J.*, vol. 243, pp. 183–187 (1987).
G. M. Olins et al., *Mol. Cell. Endocrinol.*, vol. 61, pp. 201–208 (1989).
A. A. Seymour et al., *Hypertension*, vol. 14(1), pp. 87–97 (1989).
A. M. Richards et al., *J. Clin. Endocrinol. Metab.*, vol. 72(6), pp. 1317–1322 (1991).
A. M. Richards et al., *Circulation Res.*, vol. 71(6), pp. 1501–1507 (1992).
E. P. Kromer et al., *Am. J. Hypertens.*, vol. 4(5), pp. 460–463 (1991).
D. B. Northridge et al., *Am. J. Hypertens.*, vol. 3(9), pp. 682–687 (1990).
B. P. Roques et al., *Trends in Pharmacological Sciences*, vol. 11, pp. 245–249 (1989).
C. Llorens et al., *Biochem. Biophys. Res. Commun.*, vol. 96, pp. 1710–1716 (1980).
C. Landriscina et al., *Biochem. Biophys. Acta*, vol. 205, pp. 136–142 (1970).
A. J. Trapani et al., *J. Cardiovasc. Pharmacol.*, vol. 14, pp. 419–424 (1989).
G. Waksman et al., *Proc. Natl. Acad. Sci. USA*, vol. 83, pp. 1523–1527 (1986).
B. P. Roques et al., *Proc. Natl. Acad. Sci. USA*, vol. 80, pp. 3178–3182 (1983).
G. Hilgetag et al., "Preparative Organic Chemistry", pp. 242–251 and 642, J. Wiley & Sons (1972).
Burnier et al., Clin. Pharmacol. Ther., 1991, 50, 181–191.
Richards et al., J. Cardiovasc. Pharmacol., 1992, 20, 735–741.
Pham et al., J. Pharmacol. Exp. Ther. 1993, 265(3), 1339.
Trippodo et al., J. Pharmacol. Exp. Ther., 1995, 272, 619–627.
Seymour et al., J. Pharmacol. Exp. Ther., 1993, 266(2) 872.
French et al., J. Cardiovac. Pharmacol., 1995, 26, 107–113.
Seymour et al., J. Cardiovasc. Pharmacol., 1991, 17–456–465.
Soubrier et al., Proc. Natl. Acad. Sci., 1988, 85, 9386–9390.
O'Connell et al. Clin. Sci., 1993, 85, 19–26.

*Primary Examiner*—Gary Geist
*Assistant Examiner*—Dwayne C. Jones
*Attorney, Agent, or Firm*—Synnestvedt & Lechner

[57] ABSTRACT

N-[Mercaptoacyl(amino acid or peptide)] compounds and S-lipophilic aliphatic carbonyl derivatives thereof, and pharmaceutical compositions comprising such compounds, as well as the use of these compounds as antihypertensives by the inhibition of neutral endopeptidase and/or peptidyl-dipeptidase A are disclosed. Methods for preparing the such compounds and derivatives are disclosed also.

14 Claims, 1 Drawing Sheet

N-[MERCAPTOACYL (AMINO ACID OR PEPTIDE)] COMPOUNDS AND S-LIPOPHILIC ALIPHATIC CARBONYL DERIVATIVES THEREOF AS ANTIHYPERTENSIVES

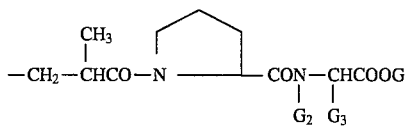

CROSS-REFERENCE OF RELATED APPLICATIONS

This is a continuation-in-part of each of the following co-pending international applications: international application Ser. No. PCT/EP92/01622, filed Jul. 17, 1992; international application Ser. No. PCT/EP92/02412, filed Oct. 21, 1992; and international application Ser. No. PCT/EP93/00147, filed Jan. 22, 1993.

FIELD OF THE INVENTION

The present invention is directed to antihypertensive compounds which function by the inhibition of neutral endopeptidase and/or peptidyldipeptidase A. This invention is directed also to the preparation of these compounds, pharmaceutical compositions containing them, and methods for their pharmaceutical use.

Reported Developments

U.S. Pat. No. 4,053,651 discloses inhibitors of peptidyl-dipeptidase A (ACE) wherein the mercapto moiety therein is substituted by hydrogen, lower alkanoyl wherein lower alkyl is defined as up to $C_7$ or benzoyl, or the mercapto moieties in two of the inhibitor molecules form a dimer by a disulfide linkage. This reference does not disclose that the ACE inhibitors also have NEP inhibitory activity.

German Patent No. DE 3,819,539 A1 discloses inhibitors of neutral endopeptidase (NEP) wherein the mercapto moiety therein is substituted by hydrogen, phenyl $C_{2-5}$ alkanoyl, thiophenyl $C_{2-5}$ alkanoyl, furanyl $C_{2-5}$ alkanoyl, pyridinyl $C_{2-5}$ alkanoyl or cycloalkyl $C_{2-5}$ alkanoyl. This reference does not disclose that the NEP inhibitors possess antihypertensive activity.

U.S. Patent No. 4,684,660 discloses inhibitors of ACE wherein the mercapto moiety therein is substituted by hydrogen or $C_{2-7}$ alkanoyl, or the mercapto moieties in two of the inhibitor molecules form a dimer by a disulfide linkage. This reference does not disclose that the ACE inhibitors also have NEP inhibitory activity.

French Patent FR 83 20024 (2,556,721) discloses inhibitors of enkephalinase wherein the mercapto moiety therein is substituted by hydrogen, $C_{2-6}$ alkanoyl or arylcarbonyl. This reference does not disclose that the NEP inhibitors possess antihypertensive activity.

U.S. Pat. No. 4,248,883 discloses inhibitors of ACE wherein the mercapto moiety therein is substituted by hydrogen, $G_4CO$—, $G_5S$— or —C(=X)—N($G_6$)($G_7$) wherein $G_4$ represents a lower alkyl group, a lower alkoxy group, a phenyl group, a substituted phenyl group, a phenyl-lower alkyl group, a substituted phenyl-lower alkyl group, a phenyl-lower alkoxy group, a substituted phenyl-lower alkoxy group, a phenoxy group, or a substituted phenoxy group; $G_5$ represents a lower alkyl group, a phenyl group, a substituted phenyl group, a phenyl-lower alkyl group, a substituted phenyl-lower alkyl group, or an amino(carboxy) lower alkyl group; $G_6$ represents a hydrogen atom or a lower alkyl group; $G_7$ represents a lower alkyl group, a phenyl group or a substituted phenyl group; X represents an oxygen or sulfur atom. This reference does not disclose that the ACE inhibitors also have NEP inhibitory activity.

U.S. Pat. No. 4,474,799 discloses inhibitors of NEP wherein the mercapto moiety therein is substituted by hydrogen, $C_{1-4}$ alkanoyl or benzoyl. This reference does not disclose that the NEP inhibitors possess antihypertensive activity.

U.S. Pat. No. 4,798,904 discloses inhibitors of NEP wherein the mercapto moiety therein is substituted by hydrogen, phenyl $C_{2-5}$ alkanoyl, substituted phenyl $C_{2-5}$ alkanoyl, thiophenyl $C_{2-5}$ alkanoyl, furanyl $C_{2-5}$ alkanoyl, or pyridinyl $C_{2-5}$ alkanoyl. This reference does not disclose that the NEP inhibitors possess antihypertensive activity.

U.S. Pat. No. 4,513,009 discloses inhibitors of NEP wherein the mercapto moiety therein is substituted by hydrogen, $C_{1-4}$ alkanoyl, halo substituted $C_{1-4}$ alkanoyl, benzhydrylcarbonyl, benzoyl, phenyl $C_{2-5}$ alkanoyl or amino $C_{2-5}$ alkanoyl. This reference does not disclose that the NEP inhibitors possess antihypertensive activity.

U.S. Pat. No. 3,246,025 discloses mercaptopropionic acid derivatives that are useful for treating drug intoxication and poisoning wherein the mercapto moiety therein is substituted by hydrogen or a radical that is readily convertible to hydrogen, e.g., benzoyl or nitrobenzoyl. This reference does not disclose that the mercaptopropionic acid derivatives possess NEP inhibitory or antihypertensive activities.

European Patent EP 0,038,758 describes compounds which are inhibitors of neutral endopeptidase (NEP). NEP is alternatively referred to as "enkephalinase" since the enzyme degrades the enkephalins which are endogenous opiate peptides or morphine receptors. These inhibitors are disclosed as useful analgesics. This reference does not disclose that NEP inhibitors possess antihypertensive activity.

In Nature, 288, 286–288 (1980), Roques et al. claim that (R,S)-(2-mercaptomethyl-3-phenylpropionyl)glycine (thiorphan) has an inhibitory power at a nanomolar concentration and behaves as an analgesic in potentiating the action of the enkephalins. This reference does not disclose that thiorphan possesses antihypertensive activity.

Other inhibitors of enkephalinase, endowed with analgesic properties, are the subject of European Patent EP 0,136,883. This reference does not disclose that the NEP inhibitors possess antihypertensive activity.

U.S. Pat. No. 4,879,309 discloses that compounds of formulae HS—$CH_2$—CH($Q_2$)—CONH—CH($Q_1$)—COO$Q_3$ and HS—$(CH_2)_m$—CH($Q_2$)—CONH—CH($Q_1$)—CO—A—COO$Q_3$ are useful for augmenting natriuresis and diuresis which thereby aids in reducing blood pressure. This reference does not disclose that the inhibitors possess antihypertensive activity separate from their natriuretic and diuretic effects.

Koehn et al., J. Biol. Chem., 262, 11623–11627 (1987) and S. L. Stephenson and A. J. Renny, Biochem. J., 243, 183–187 (1987) have reported that auricular natriuretic peptide which is liberated by the heart, particularly in cardiac insufficiency, and which augments natriuretic, diuretic and vasodilator effects, is inactivated by the peripheral enzyme EP 24.11. Thus, the inhibitor of NEP, thiorphan, and certain of its derivatives are capable of augmenting the half-life of circulating auricular natriuretic peptide and thereby aids in reducing blood pressure in the rat. [G. Olins et al., *Moll. Cell. Endocrinol.*, 61, 201–208 (1989); A. A. Seymour et al., Hypertension, 14, 87–97 (1989)]. However, none of these references disclose that the NEP inhibitors possess ACE inhibition mediated antihypertensive properties exhibited by inhibitors of ACE activity.

Furthermore, in clinical trials, the inhibitors of neutral endopeptidase, such as thiorphan, produce natriuresis and diuresis without any significant hypotensive effect, except in certain sick people showing cardiac or renal insufficiency. A. M. Richards et al., *J. Clin. Endocrinol. Metab.*, 72, 1317–1322 (1991); A.M. Richards et al., *Circulation Res.*, 71, 1501–1507 (1992); E. P. Kromer et al., *Am. J. Hypertens.*, 4, 460–463 (1991); D. B. Northridge et al., *Am. J. Hypertens.*, 3, 682–687 (1990).

B. P. Roques et al., *Trends in Pharmacological Sciences*, 11(6) (1989), suggested combining in one molecule the properties of inhibition (1) of NEP, in order to potentiate the natriuretic, diuretic and vasorelaxant effects of atrial natriuretic peptide, and (2) of ACE, to block the hypertensive effects induced by angiotensin II formation. The reference does not disclose molecules capable of acting with both of these two enzymes at low concentrations.

SUMMARY OF THE INVENTION

One aspect of the present invention relates to an S-lipophilic aliphatic carbonyl [N-mercaptoacyl(amino acid or peptide)] compound.

Another aspect of the present invention relates to a compound of the formula $$R—S—X \quad (I)$$

wherein:

X is a residue of the formula

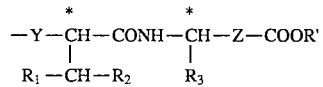

(II)

Y is a chemical single bond or —CH$_2$—;

Z is a chemical bond or

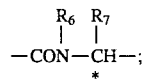

R is hydrogen, acyl, aroyl, cycloalkylcarbonyl, lipophilic aliphatic carbonyl or —S—X;

R$_1$ is hydrogen or alkyl;

R$_2$ is hydrogen, alkyl, aryl, heteroaryl, aralkyl, alkoxy, alkoxy-lower alkyl, or aralkyloxy;

R$_1$ and R$_2$ are also linked together to form aryl;

when R$_2$ is aryl, heteroaryl, aralkyl or aralkyloxy, R$_1$ is also alkylene which is linked to R$_2$ to form fused aromatic cycloalkyl;

R$_3$ is hydrogen, alkyl, aryl, alkoxy, aryloxy or —CH(R$_4$)(R$_5$), where R$_4$ has the same definition as R$_1$ and R$_5$ has the same definition as R$_2$;

R$_6$ is hydrogen or alkyl;

R$_7$ is cycloalkyl, aralkyl, aryloxy-lower alkyl or alkoxy-lower alkyl;

R$_6$ and R$_7$ are also linked together to form, together with the nitrogen and carbon atoms to which R$_6$ and R$_7$ are respectively attached, heterocyclyl;

R' is hydrogen, alkyl, aralkyl, acyl, aroyl or lipophilic aliphatic carbonyl, with the proviso that when R$_1$ is hydrogen or methyl, R$_3$ is —CH(R$_4$)(R$_5$) wherein one of R$_4$ and R$_5$ is hydrogen, methyl, n-propyl or i-propyl and the other of R$_4$ and R$_5$ is hydrogen or methyl and Z is —CON(R$_6$)—CH(R$_7$)—wherein R$_6$ and R$_7$ are linked together to form, together with the nitrogen and carbon atoms to which R$_6$ and R$_7$ are respectively attached, prolinyl, hydroxyprolinyl, methoxyprolinyl or thiazolidinyl, then R$_2$ is not hydrogen, alkyl of 1 to 5 carbon atoms, unsubstituted phenyl or unsubstituted benzyl;

or a pharmaceutically acceptable salt thereof.

Yet another aspect of the present invention relates to methods for the preparation of the aforementioned compounds.

Still another aspect of the present invention relates to pharmaceutical compositions comprising, in admixture with a pharmaceutically acceptable carrier, an antihypertensive amount of the aforementioned compounds.

Yet another aspect of the present invention relates to methods of treating hypertension in mammals comprising administering an effective antihypertensive amount of the above compounds.

Compounds within the scope of the present invention inhibit neutral endopeptidase (NEP) and/or peptidyldipeptidase A (ACE) and are useful in treating hypertension; preferably by inhibiting both ACE and NEP.

DETAILED DESCRIPTION OF THE INVENTION

Figure 1:
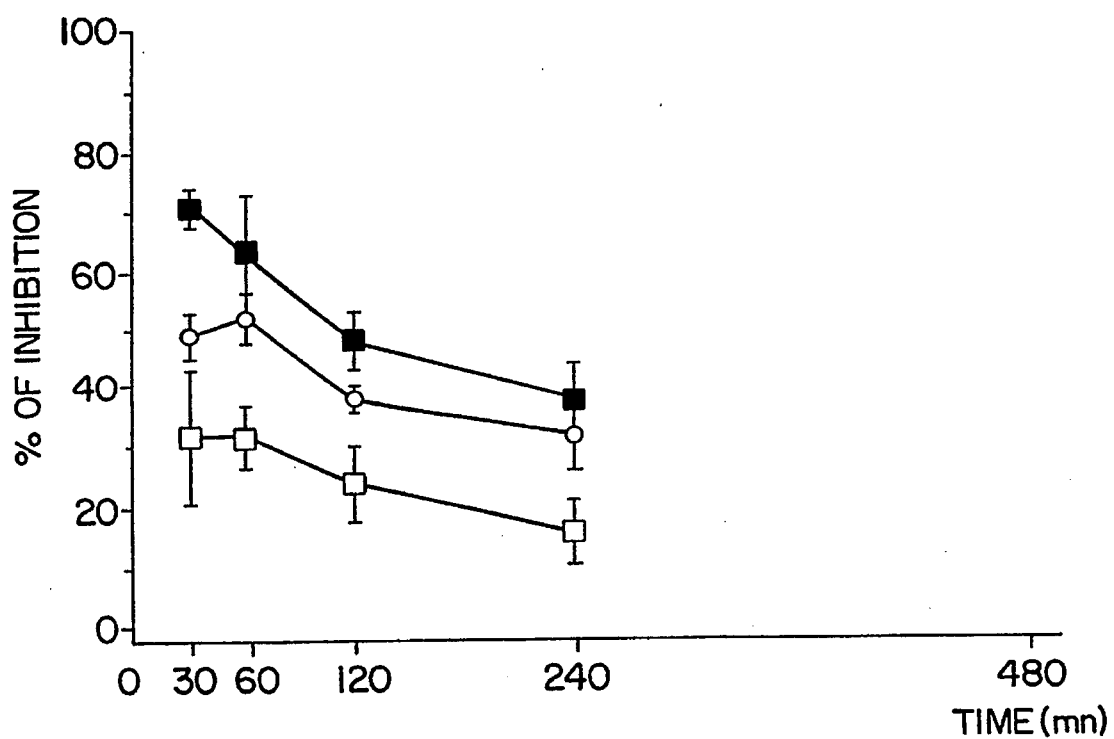
FIG. 1 is a time course plot of the percent of in vivo inhibition of ACE by the following mixed NEP/ACE inhibitors: N-(2-acetylthiomethyl-1-oxo-3-phenylbutyl)alanine as a mixture of four stereoisomers (-□-); N-(2-adamantylthiomethyl-1-oxo-3-phenylbutyl)alanine as a mixture of four stereoisomers (-O-); and N-(2-adamantylthiomethyl-1-oxo-3-phenylbutyl)alanine as a single stereoisomer (-■-)at a dose of 2.6×10$^{-5}$ mole/Kg p.o.

As employed above and throughout the disclosure, the following terms, unless otherwise indicated, shall be understood to have the following meanings:

"Patient" embraces both human beings and other mammals.

The "*" designation on the carbons in the compounds according to the invention represents that the carbons are chiral.

"Alkyl" means an aliphatic hydrocarbon group which may be straight or branched having about 1 to about 20 carbon atoms in the chain. "Lower alkyl" means alkyl having about 1 to about 8 carbon atoms. "Higher alkyl" means alkyl having about 10 to about 20 carbon atoms. The alkyl may be optionally substituted with one or more alkyl group substituents which may be the same or different, where "alkyl group substituent" includes halo, aryl, hydroxy, alkoxy, aryloxy, alkyloxy, alkylthio, arylthio, aralkyloxy, aralkylthio, carboxy alkoxycarbonyl, oxo and cycloalkyl. "Branched" means that a lower alkyl group such as methyl, ethyl or propyl is attached to a linear alkyl chain. Exemplary alkyl groups include methyl, ethyl, i-propyl, n-butyl, t-butyl, n-pentyl, heptyl, octyl, decyl and dodecyl. Exemplary substituted alkyl groups include cyclohexylmethyl and trifluoromethyl. Preferred alkyl groups include the lower alkyl groups.

"Alkenyl" means an alkyl group containing a carbon-carbon double bond. "Lower alkenyl" means alkenyl having about 1 to about 8 carbon atoms. "Higher alkenyl" means alkenyl having about 10 to about 20 carbon atoms. The alkenyl may be optionally substituted with one or more "alkyl group substituents". Exemplary alkenyl groups include vinyl, allyl, n-pentenyl, decenyl, dodecenyl and tetradecadienyl. Preferred alkenyl groups include the lower alkenyl groups.

"Alkynyl" means an alkyl group containing a carbon-carbon triple bond. "Lower alkynyl" means alkynyl having about 1 to about 8 carbon atoms. "Higher alkynyl" means alkynyl having about 10 to about 20 carbon atoms. The alkynyl may be optionally substituted with one or more "alkyl group substituents". Exemplary alkynyl groups include ethynyl, propargyl, n-pentynyl, decynyl and dodecynyl. Preferred alkynyl groups include the lower alkynyl groups.

"Cycloalkyl" means a non-aromatic mono- or multicyclic ring system of about 4 to about 10 carbon atoms. The cycloalkyl may be optionally partially unsaturated. The cycloalkyl may be also optionally substituted with an aryl group substituent, oxo and/or alkylene. Preferred monocyclic cycloalkyl rings include cyclopentyl, cyclohexyl and cycloheptyl. Preferred multicyclic cycloalkyl rings include adamantyl, octahydronaphthyl, decalin, camphor, camphane, noradamantyl, norbornane, bicyclo[2.2.2.]-oct-5-ene, cis-5-norbornene, 5-norbornene, (1R)-(−)-myrtentane, norbornane and anti-3-oxo-tricyclo[2.2.1.0$^{2,6}$]-heptane.

"Alkyloxymethyl" means an alkyl—O—CH$_2$— group wherein alkyl is as previously described. Exemplary alkyloxymethyl groups include methoxymethyl, ethoxymethyl, n-propoxymethyl, i-propoxymethyl, n-butoxymethyl and heptoxymethyl. When $R_7$ in the compound of formula (V) herein is alkyloxymethyl, it is preferred that the alkyl contains about 1 to about 6 carbon atoms.

"Aryl" means an aromatic carbocyclic radical containing about 6 to about 10 carbon atoms. The aryl may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NQQ', where Q and Q' are each independently hydrogen, alkyl, aryl and aralkyl. Exemplary aryl include substituted or unsubstituted phenyl and substituted or unsubstituted naphthyl.

"Heteroaryl" means a monocyclic or multicyclic ring system of about 5 to about 10 members wherein one or more of the atoms in the ring system is an element other than carbon, for example, nitrogen, oxygen and sulfur. The heteroaryl may be optionally substituted by one or more aryl group substituents. Exemplary heteroaryl groups include furanyl, thienyl, pyridyl, pyrrolyl, N-methylpyrrolyl, quinolinyl, and isoquinolinyl.

"Heterocyclyl" means a monocyclic or multicyclic ring system of about 4 to about 10 members wherein one or more of the atoms in the ring system is an element other than carbon, for example, nitrogen, oxygen and sulfur. The heterocyclyl may be optionally substituted by one or more alkyl group substituents or alkylene. Exemplary heterocyclyl moieties include quinuclidine,

and

Preferred substituents of the heterocyclyl include hydroxy, alkoxy containing about 1 to about 4 carbon atoms, trifluoromethyl, fluorine, and alkylene of about 3 to about 4 carbon atoms which alkylene, when substituted on the heterocyclyl, forms a saturated or unsaturated hydrocarbon ring having about 5 to about 6 members.

"Acyl" means an alkyl—CO— group wherein alkyl is as previously described. Preferred acyl comprise alkyl of about 1 to about 3 carbon atoms. Exemplary acyl groups include acetyl, propanoyl, 2-methylpropanoyl, butanoyl and palmitoyl.

"Aroyl" means an aryl—CO— group wherein aryl is as described previously. Exemplary groups include benzoyl and 1- and 2-naphthoyl.

"Alkoxy" means an alkyl—O—group wherein alkyl is as described previously. Exemplary alkoxy groups include methoxy, ethoxy, n-propoxy, i-propoxy, n-butoxy and heptoxy.

"Aryloxy" means an aryl—O—group wherein the aryl group is as described previously. Exemplary aryloxy groups include phenoxy and naphthoxy. "Alkylthio" means an alkyl—S— group wherein alkyl is as described previously. Exemplary alkylthio groups include methylthio, ethylthio, i-propylthio and heptylthio. "Arylthio" means an aryl—S— group wherein the aryl group is as described previously. Exemplary arylthio groups include phenthio and naphththio. "Aralkyl" means an aryl-alkyl- group wherein aryl and alkyl are as described previously. Exemplary aralkyl groups include benzyl, phenylethyl and naphthylmethyl. "Aralkyloxy" means an aralkyl—O—group wherein the aralkyl group is as described previously. An exemplary aralkyloxy group is benzyloxy. "Aralkylthio" means an aralkyl—S— group wherein the aralkyl group is as described previously. An exemplary aralkylthio group is benzylthio. "Dialkylamino" means an —NQQ' group wherein both Q and Q' are each independently alkyl groups as described previously. Exemplary alkylamino groups include ethylmethylamino, dimethylamino and diethylamino. "Alkoxycarbonyl" means an alkyl—O—CO— group. Exemplary alkoxycarbonyl groups include methoxy- and ethoxy-carbonyl. "Aryloxycarbonyl" means an aryl—O—CO— group. Exemplary aryloxycarbonyl groups include phenoxy- and naphthoxy-carbonyl. "Aralkoxycarbonyl" means an aralkyl—O—CO— group. An exemplary aralkoxycarbonyl group is benzyloxycarbonyl. "Carbamoyl" means an H$_2$N—CO— group.

"Alkylcarbamoyl" means a Q'QN—CO— group wherein one of Q and Q' is hydrogen and the other of Q and Q' is alkyl as described previously.

"Dialkylcarbamoyl" means a Q'QN—CO— group wherein Q and Q' are each independently alkyl as described previously.

"Acyloxy" means an acyl—O—group wherein acyl is as described previously.

"Acylamino" means an acyl—NH— group wherein acyl is as described previously.

"Aroylamino" means an aroyl—NH— group wherein aroyl is as described previously.

"Alkylene" means a straight or branched bivalent hydrocarbon chain group having from about 1 to about 8 carbon atoms. The alkylene group may be also optionally unsaturated. There may be optionally inserted along the alkylene group one or more oxygen, sulphur or substituted nitrogen atoms, wherein the nitrogen substituent is alkyl as described previously. Exemplary alkylene groups include ethylene (—CH$_2$CH$_2$—), propylene (—CH$_2$—)$_3$, —CH=CH—CH=CH—, —CH=CH—CH$_2$—, —CH$_2$N(CH$_3$)—CH$_2$—, -methylenedioxy (—O—CH$_2$—O—) and ethylenedioxy (—O—(CH$_2$—)$_2$—O—). It is preferred that the alkylene group has about 2 to about 3 carbon atoms.

"Halo" means fluoro, chloro or bromo.

The symbol "φ" means phenyl.

"Amino Acid" may be naturally occurring or synthetic. Exemplary amino acids include proline, hydroxyproline, 4,4-ethylenedioxyproline, methoxyproline, thiazolidinecarboxylic acid, tryptophane, glycine alanine, leucine, isoleucine, valine, tyrosine, O-benzylserine, 2-carboxylpiperidine, 1-amino-1-phenylacetic acid and 1-amino-1-indan-2-ylacetic acid.

"Peptide" may be about 2 to about 6 amino acid residues bonded by peptide linkages. Peptides having about 2 to about 3 amino acid residues are preferred.

"Lipophilic aliphatic carbonyl radical" means higher alkyl carbonyl, higher alkenyl carbonyl, higher alkynyl carbonyl, multicycloalkyl carbonyl or multicyclic heterocyclyl carbonyl wherein the alkyl, alkenyl, alkynyl, cycloalkyl and heterocyclyl are as described previously. Multi cycloalkyl carbonyl radicals are preferred, and more preferred are the multi cycloalkyl carbonyl radicals wherein the multi cycloalkyl moiety thereof has bridging carbons, for example, adamantane, camphor and norbornane. Exemplary lipophilic aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(–)-myrtentaneacetyl, 2-norbornaneacetyl, anti-3-oxo-tricyclo[2.2.1.0$^{2,6}$]-heptane-7-carbonyl, decanoyl, dodecanoyl, dodecenoyl, tetradecadienoyl, decynoyl or dodecynoyl.

"Product" means the active compounds of the invention in their free acid, free base and/or salt forms.

Various of the developments which are the subject of the present application are the subject also of international application Serial No. PCT/EP92/01622, filed Jul. 17, 1992 (hereinafter "international application No. 1"); international application Serial No. PCT/EP92/02412, filed Oct. 21, 1992 (hereinafter "international application No. 2"); and international application Serial No. PCT/EP93/00147, filed Jan. 22, 1993 (hereinafter "international application No. 3"), each of said international applications being incorporated herein by reference. (The three aforementioned international applications are collectively referred to hereinafter as "the international applications".) The various developments of the present application and the corresponding international applications are discussed more fully hereinafter.

Subject Matter of the Development Which is Described in International Application No. 1

In connection with the subject matter of the development which is described also in international application No. 1, compounds of formula (I) above constitute a class of compounds for use in the practice of the present invention wherein:

X is a residue of formula (II) above where Y is a chemical bond and Z is $$-CON(R_6)-\overset{*}{C}H(R_7)-;$$

R is hydrogen, acyl, benzoyl, adamantoyl or —S—X;

$R_1$ is hydrogen or methyl;

$R_2$ is hydrogen, alkyl, phenyl, benzyl, alkoxy, alkyloxymethyl or benzyloxy;

$R_1$ and $R_2$ are also linked together to form phenyl;

when $R_2$ is phenyl, benzyl or benzyloxy, $R_1$ is also alkylene which is linked to $R_2$ to form benzocycloalkyl;

$R_3$ is —CH($R_4$)($R_5$), where $R_4$ has the definition of $R_1$ and $R_5$ has the definition of $R_2$;

$R_6$ is hydrogen or methyl;

$R_7$ is cyclopentyl, α-naphthylmethyl, β-naphthylmethyl, benzyl, phenoxymethyl or alkoxymethyl;

$R_6$ and $R_7$ are also linked together to form, together with the nitrogen and carbon atoms to which $R_6$ and $R_7$ are respectively attached, heterocyclyl; and R' is hydrogen, methyl, ethyl, benzyl, cyclohexylmethyl or palmitoyl, with the proviso that when $R_1$ is hydrogen or methyl, one of $R_4$ and $R_5$ is hydrogen, methyl, n-propyl or i-propyl and the other of $R_4$ and $R_5$ is hydrogen or methyl, and $R_6$ and $R_7$ are linked together to form, together with the nitrogen and carbon atoms to which $R_6$ and $R_7$ are respectively attached, prolinyl, hydroxyprolinyl, methoxyprolinyl or thiozolidinyl, then $R_2$ is not hydrogen, alkyl of 1 to 5 carbon atoms, unsubstituted phenyl or unsubstituted benzyl.

Stated another way, the compounds of the present development involve compounds of formula (I), wherein X, Y, Z, R, $R_1$, $R_2$, $R_3$, $R_4$, $R_5$, $R_6$, $R_7$ and R' are as described above, with the proviso that when $R_1$ is hydrogen or methyl, $R_3$ and the moiety $$-NH-\underset{|}{CH}-CO-$$

to which $R_3$ is attached together form alaninyl, leucinyl, valinyl or isoleucinyl, and $R_6$ and $R_7$ are linked together for form, together with the nitrogen and carbon atoms to which $R_6$ and $R_7$ are respectively attached, prolinyl, hydroxyprolinyl, methoxyprolinyl or thiazolidinyl, then $R_2$ is not hydrogen, alkyl of 1 to 5 carbon atoms, unsubstituted phenyl or unsubstituted benzyl.

A preferred class of compounds of the present development which are useful in the practice of the invention are described by the formula $$R-S-\overset{*}{C}H-CONH-\overset{*}{C}H-CO\underset{|}{N}-\overset{R_6}{\underset{|}{C}H}-\overset{*}{COOR'} \quad (III)$$
$$\phantom{R-S-}\underset{|}{R_1-CH-R_2}\phantom{-CONH-}\underset{|}{CH-R_5}$$
$$\phantom{R-S-CH-CONH-CH-CON-CH}\underset{|}{R_4}$$

wherein:

R is hydrogen;

$R_1$ and $R_4$ are each independently hydrogen or methyl;

$R_2$ and $R_5$ are each independently alkyl, alkoxy, phenyl, benzyl or benzyloxy;

$R_1$ and $R_2$ groups and $R_4$ and $R_5$ groups are also each independently linked together to form phenyl;

when $R_2$ and $R_5$ are each independently phenyl, benzyl or benzyloxy, $R_1$ and $R_4$ are also each independently alkylene which is linked respectively to $R_2$ and $R_5$ to form indanyl;

$R_7$ is benzyl in which the phenyl ring is optionally substituted with hydroxy, or $R_6$ and $R_7$ are linked together to form, together with the nitrogen and carbon atoms to which $R_6$ and $R_7$ are respectively attached, saturated heterocyclyl of 5 or 6 members; and R' is hydrogen.

Compounds according to the development described herein contain several asymmetric centers and may exist in the form of pure stereoisomers or in the form of mixtures of stereoisomers. Preferred compounds are those wherein the carbon atoms of the principal chain marked by an asterisk (*) have the L configuration.

Subject Matter of the Development Which is Described in International Application No. 2

In connection with the subject matter of the development which is described also in international application No. 2, compounds of formula (I) above constitute a class of compounds for use in the practice of the present invention wherein:

X is a residue of formula (II) above where Y is —$CH_2$— and Z is a chemical single bond;

R is hydrogen, unbranched- or branched-chain acyl of 2 to 18 carbon atoms, aroyl in which the aryl portion contains 6 to 10 carbon atoms, cycloalkylcarbonyl in which the cycloalkyl portion contains 4 to 10 carbon atoms, or —S—X;

$R_1$ is unbranched- or branched-chain alkyl of 1 to 8 carbon atoms which is optionally substituted with one or more alkyl group substituents;

$R_2$ is aryl or heteroaryl of 5 to 10 carbon atoms, and is optionally substituted with one or more aryl group substituents at a position other than the position which is ortho to the point of attachment of $R_2$;

$R_1$ is also an unbranched- or branched-chain alkylene containing 2 to 8 carbon atoms which is linked to a carbon atom of $R_2$ that is at a position which is ortho to the point of attachment of $R_2$ to the methine (CH) group, and wherein the alkylene chain optionally contains one or more substituted nitrogen, oxygen or sulphur atoms;

$R_3$ is hydrogen; unbranched- or branched-chain alkyl of 1 to 8 carbon atoms which is optionally substituted with one or more alkyl group substituents; aryl or heteroaryl of 5 to 10 carbon atoms which is optionally substituted with one or more aryl group substituents; alkoxy of 1 to 8 carbon atoms wherein the alkyl portion is optionally substituted with one or more alkyl group substituents; or aryloxy of 6 to 10 carbon atoms wherein the aryl portion is optionally substituted with one or more aryl group substituents; and R' is hydrogen, unbranched- or branched-chain alkyl of 1 to 8 carbon atoms, aralkyl in which the aryl portion contains 6 to 10 carbon atoms and in which the alkyl portion, which is unbranched- or branched-chain, contains 1 to 8 carbon atoms, acyl of 2 to 18 carbon atoms or aroyl in which the aryl portion contains 6 to 10 carbon atoms and is optionally substituted with one or more aryl group substituents.

A preferred class of compounds of the present development which are useful in the practice of the invention are described by the formula X is a residue of the formula

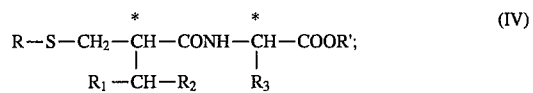

wherein:

R is hydrogen, acyl of 2 to 4 carbon atoms, benzoyl in which the phenyl ring is optionally substituted with halo, hydroxy, alkoxy of 1 to 4 carbon atoms, trifluoromethyl, amino or dialkylamino in which each alkyl portion is independently alkyl of 1 to 4 carbon atoms, adamantoyl, palmitoyl, pamoyl or —S—X;

$R_1$ is methyl or trifluoromethyl;

$R_2$ is phenyl or heteroaryl which is 2-, 3- or 4-pyridyl, or N-methyl-2- or -3-pyrrolyl, wherein (A) said phenyl or heteroaryl is optionally substituted with one or more substituents at a position other than the position which is ortho to the point of attachment of $R_2$ to the methine (CH) group, said substituents being independently halo, hydroxy, unbranched- or branched-chain acyloxy of 1 to 4 carbon atoms, unbranched- or branched-chain alkoxy of 1 to 4 carbon atoms, phenoxy, phenylthio, amino, dialkylamino in which each alkyl portion is independently 1 to 4 carbon atoms, methylenedioxy or ethylenedioxy, or (B) said phenyl or heteroaryl is connected to $R_1$ which is alkylene of 2 or 3 carbon atoms and which is linked to a carbon atom of $R_2$ at a position that is ortho to the point of attachment of $R_2$ to the methine (CH) group, said alkylene being optionally substituted with methyl, and wherein said alkylene may contain also, in the alkylene chain, one or more —$CH_2$—W— or —W—$CH_2$— diradicals, wherein W is —O—, —S— or —N($CH_3$)—;

$R_3$ is hydrogen, trifluoromethyl, unbranched- or branched-chain alkyl of 1 to 8 carbon atoms which is optionally substituted with one or more of phenyl, hydroxy, alkoxy of 1 to 4 carbon atoms, phenoxy, alkylthio of 1 to 4 carbon atoms, phenylthio, benzyloxy or benzylthio, alkoxy of 1 to 8 carbon atoms, phenoxy or aryl, such as phenyl or thienyl, and wherein phenyl and aryl, and the phenyl portions of phenoxy, phenylthio, benzyloxy and benzylthio, are optionally substituted with one or more of halo, hydroxy, alkoxy of 1 to 4 carbon atoms, amino, dialkylamino in which each alkyl portion is independently 1 to 4 carbon atoms, methylenedioxy or ethylenedioxy; and R' is hydrogen, methyl, ethyl, benzyl, cyclohexylmethyl, palmitoyl or pamoyl.

Compounds of the present development contain several asymmetric centers and may exist in the form of pure stereoisomers or in the form of mixtures of stereoisomers. As noted hereinbefore, the carbon atoms marked by an asterisk (*) designate asymmetric centers. In the compounds of the present development, unless stated otherwise, designations regarding the stereochemical configurations at the carbon atoms marked by an asterisk relate: first to the carbon atom bearing the substituents $R_1$ and $R_2$; second to central carbon atom of the propanoyl chain; and third to the carbon atom bearing the substituent $R_3$. Preferred compounds of the present development include those wherein any of the carbon atoms marked by an asterisk (*) have the S configuration. Preferred also include compounds having a stereochemical designation selected from the group consisting of R,R,S, S,R,S, S,S,S and R,S,S, and more preferred compounds have a stereochemical designation of S,S,S or R,S,S.

Subject Matter of the Development Which is Described in International Application No. 3

In connection with the subject matter of the development which is described also in international application No. 3, N-mercaptoacyl(amino acid or peptide) compounds which are derivatized with an S-lipophilic aliphatic carbonyl group constitute a class of compounds for use in the practice of the present invention.

Exemplary N-mercaptoacyl(amino acid or peptide) compounds, which are derivatized by an S-lipophilic aliphatic carbonyl group to form the compounds of the present development, include the N-mercaptoacyl(amino acid or peptide) compounds disclosed in the following publications: U.S. Pat. Nos. 4,053,651; 4,684,600; 4,248,883; 4,474,799; 4,798,904; 4,513,009; and 4,879,309; German Patent No. DE 3,819,539 A1; French Patent No. FR 83 20024 (2,556, 721); European Patent Nos. EP 0 038 758; and 0 136 883; international application Nos. 1 and 2; and Nature, 288, 286–288 (1980). These references are incorporated by reference herein. Various compounds of formulae (I) which are described throughout the present specification where R is hydrogen, are exemplary N-mercaptoacyl(amino acid or peptide) compounds for derivatizing with S-lipophilic aliphatic carbonyl groups also.

Preferred mercaptoalkanoyl (amino acid or peptide) species, which can be derivatized by an S-lipophilic aliphatic carbonyl group to form the compounds according to the present development, include those in Tables I and II herein and the following species:

N-(2-mercaptomethyl-1-oxo-3-phenylbutyl)tyrosine; N-(2-mercaptomethyl-1-oxo-3-phenylbutyl)glycine; N-(2-mercaptomethyl-1-oxo-3-phenylbutyl)-O-benzylserine; N-(2-mercaptomethyl-1-oxo-3-phenylbutyl)alanine; N-(2-mercaptomethyl-1-oxo-3-phenylbutyl)norleucine; N-[3-mercapto-2-(1-indanyl)-1-oxopropyl]alanine; N-[2-mercaptomethyl-3-(4-hydroxyphenyl)-1-oxobutyl]alanine; N-[2-(1-mercaptomethyl-3-(4-hydroxyphenyl)-1-oxobutyl)]tyrosine; N-[N'-(2-mercapto-3-phenylpropanoyl)valyl]tyrosine; N-[N'-(2-mercapto-3-phenylpropanoyl)isoleucinyl]tyrosine; N-[N'-(2-mercapto-3-phenylpropanoyl)isoleucinyl]piperidin-2-oic acid; N-[N'-(2-mercapto-3-phenylpropanoyl)n-leucinyl]tyrosine; N-[N'-(2-mercapto-3-phenylpropanoyl)leucinyl]tyrosine; N-[N'-(2-mercapto-3-methylpentanoyl)phenalanyl]tyrosine; N-[N'-(2-mercapto-3-methylpentanoyl)valyl]tyrosine; N-[N'-(2-mercapto-4-phenylbutanoyl)valyl]tyrosine; N-[N'-(2-mercapto-3-methylbutanoyl)isoleucinyl]tyrosine; N-[N'-(2-mercapto-2phenylacetyl)isoleucinyl]tyrosine; N-[N'-(2-mercapto-3methylpentanoyl)isoleucinyl]tyrosine; N-[N'-(2-mercapto-3-methylpentanoyl)-2-amino-3-methoxybutanoyl]tyrosine; N-[N'-(2-mercapto-3-methoxypentanoyl)-2-amino-3-methoxybutanoyl]proline; N-[N'-(2-mercapto-3-methoxypentanoyl)-2-amino-3methoxybutanoyl]hydroxyproline; N-[N'-(2-mercapto-3-methylpentanoyl)-2-amino-3-benzyloxybutanoyl]tyrosine; N-[N'-(2-mercapto-3-methylbutanoyl)-2-amino-3-methylbutanoyl]tyrosine; N-[N'-(2-mercapto-3-methylpentanoyl)-2-amino-3-methoxybutanoyl]tyrosine; N-[N'-(2-mercapto-3-methylbutanoyl)-2-amino-3-benzyloxybutanoyl]tyrosine; N-[N'-(2-mercapto-3-methylbutanoyl)-2-amino-3-benzyloxybutanoyl]proline; N-[N'-(2-mercapto-3-methylbutanoyl)isoleucinyl]tyrosine; N-[N'-(2-mercapto-3-methoxybutanoyl)-3-methylphenalanyl]tyrosine; N-[N'-(2-mercapto-3-methoxybutanoyl)-2-amino-2-indan-2'-ylacetyl]tyrosine; N-[N'-(2-mercapto-3-benzyloxybutanoyl)isoleucinyl]tyrosine; N-[N'-(2-mercapto-2-phenylacetyl)valinyl]tyrosine; N-[N'-(2-mercapto-2-indan-2'-yl)isoleucinyl]tyrosine; N-[N'-(2-mercapto-3-methylpentanoyl)-2-amino-2-phenylacetyl]tyrosine; N-[N'-(2-mercapto-3-methylbutanoyl)-2-amino-2-phenylacetyl]tyrosine; N-[N'-(2-mercapto-3-methylbutanoyl)-2-amino-2-phenylacetyl]piperidin-2 2-oic acid; N-[N'-(2-mercapto-3-methylpentanoyl)-2-amino-2-phenylacetyl]tyrosine; N-[N'-(2-mercapto-3-methylpentanoyl)alanyl]piperidin-2-oic acid; N-[N'-(2-mercapto-3-methylbutanoyl)-2-amino-2-phenylacetyl]piperidin-2-oic acid; N-[N'-(2-mercapto-2-phenylacetyl)-2-amino-2-phenylacetyl]tyrosine; N-[N'-(2-mercapto-2-phenylacetyl)-2-amino-3-phenylbutanoyl]tyrosine; N-[N'-(2-mercapto-2-phenylacetyl)-2-amino-3-ethoxybutanoyl]tyrosine; and N-[N'(2-mercapto-2-phenylacetyl)valinyl]tyrosine.

TABLE I

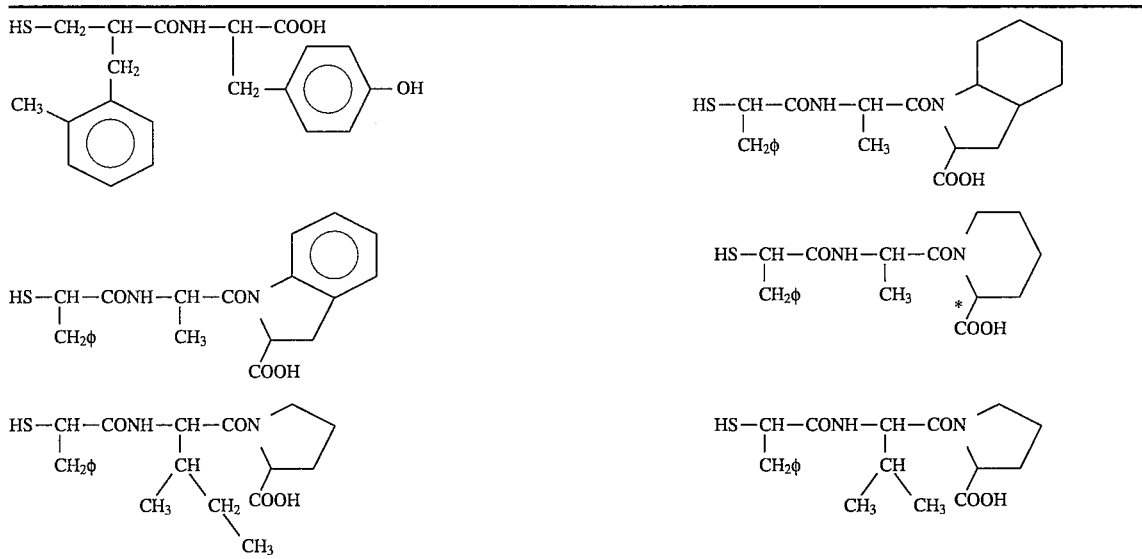

TABLE I-continued
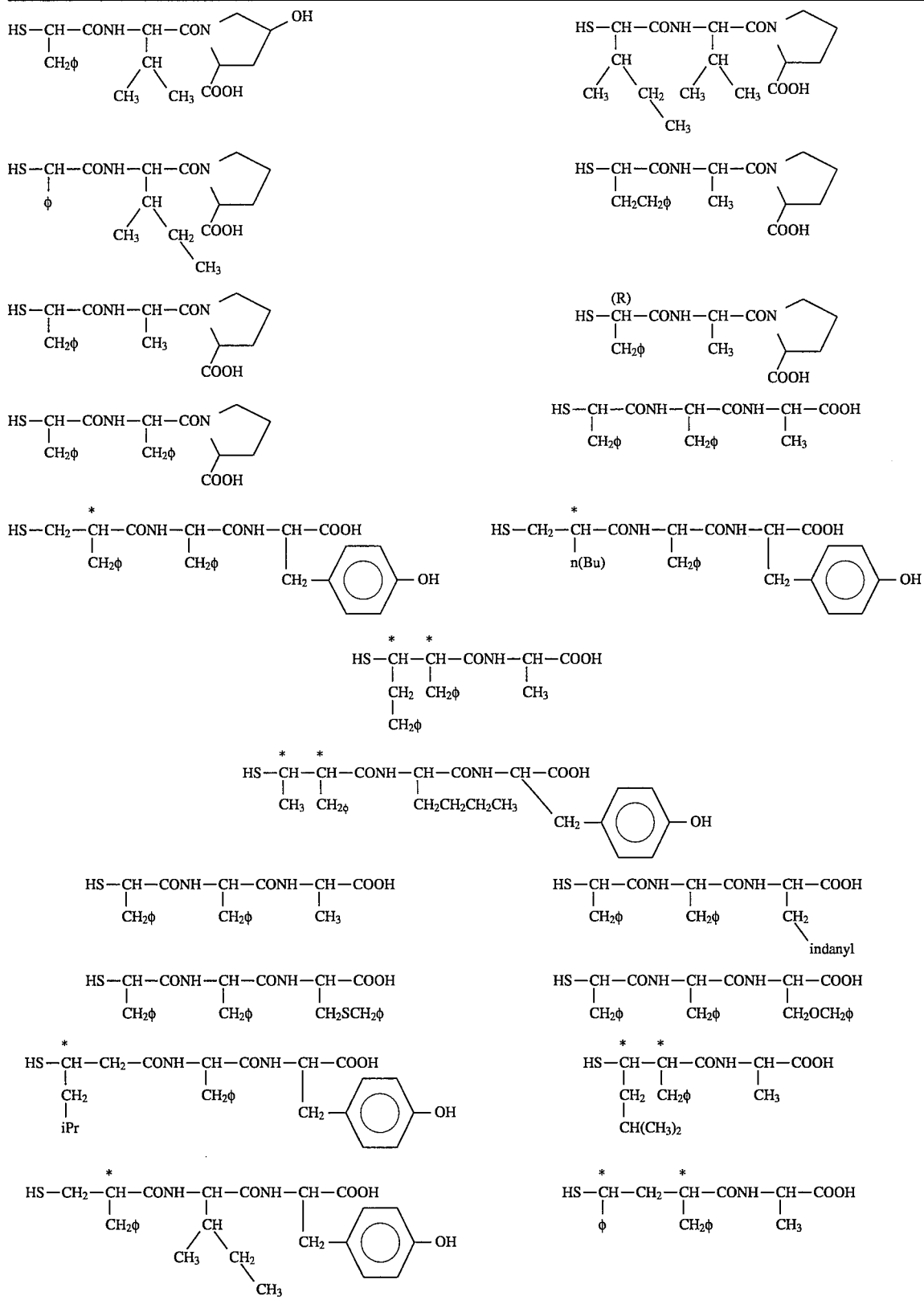

Compounds described by formula (IV) above constitute a class of the aforementioned S-lipophilic aliphatic carbonyl compounds of the present development which are useful in the practice of the present invention wherein:

R is lipophilic aliphatic carbonyl;

$R_1$ is alkyl;

$R_2$ is aryl or heteroaryl;

$R_1$ is also alkylene which is linked to $R_2$;

$R_3$ is hydrogen, alkyl, aryl, alkoxy or aryloxy;

R' is hydrogen, alkyl, aralkyl, acyl or aroyl;

or a pharmaceutically acceptable salt thereof.

R, when alkylene, is preferably linked to a carbon atom of $R_2$ that is at a position which is ortho to the point of attachment of $R_2$ to the methine (CH) group.

A preferred class of compounds of the present development which are useful in the practice of the invention include those described by formula (IV) wherein:

R is higher alkylcarbonyl or multi-cycloalkyl carbonyl;

$R_1$ is lower alkyl or alkylene which is linked to $R_2$;

$R_2$ is aryl or heteroaryl;

$R_3$ is hydrogen, lower alkyl, aryl, heteroaryl, lower alkoxy or aryloxy; and

R' is hydrogen, lower alkyl, aryl-lower alkyl, acyl or aroyl.

A more preferred class of compounds of the present development include those of formula (IV) wherein:

R is adamantoyl or palmitoyl;

$R_1$ is methyl, trifluoromethyl or —$CH_2$—W—, —W—$CH_2$— or alkylene of 2 to 3 carbon atoms which is substituted with methyl and which is linked to $R_2$, wherein W is —O—, —S— or —N($CH_3$)—;

$R_2$ is phenyl or heteroaryl which is 2-, 3- or 4-pyridyl, or N-methyl-2- or -3-pyrolyl, said phenyl or heteroaryl being unsubstituted or substituted with one or more of halo, hydroxy, acyloxy of 1 to 4 carbon atoms, alkoxy of 1 to 4 carbon atoms, phenoxy, phenylthio, amino, dialkylamino in which each alkyl portion is alkyl of 1 to 4 carbon atoms, methylenedioxy or ethylenedioxy;

$R_3$ is hydrogen, trifluoromethyl, alkoxy of 1 to 8 carbon atoms, phenoxy, phenyl, thienyl or alkyl of 1 to 8 carbon atoms which is optionally substituted with phenyl, hydroxy, alkoxy of 1 to 4 carbon atoms, phenoxy, alkylthio of 1 to 4 carbon atoms, phenylthio, benzyloxy or benzylthio, wherein phenyl and the phenyl portions of phenoxy, phenylthio, benzyloxy and benzylthio are optionally substituted with one or more of halo, hydroxy, alkoxy of 1 to 4 carbon atoms, amino, dialkylamino in which each alkyl portion is alkyl of 1 to 4 carbon atoms, methylenedioxy or ethylenedioxy; and R' is hydrogen, methyl, ethyl, benzyl, cyclohexylmethyl, palmitoyl or pamoyl.

Compounds described by formula (V) below constitute another class of the aforementioned S-lipophilic aliphatic carbonyl compounds of the present development which are useful in the practice of the invention:

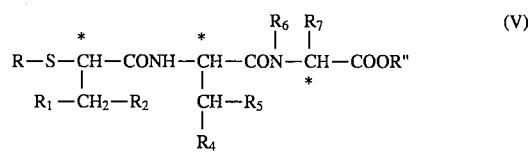

wherein:

R is lipophilic aliphatic carbonyl;

$R_1$ and $R_4$ are each independently hydrogen or alkyl;

$R_2$ and $R_5$ are each independently hydrogen, alkyl, aryl, aralkyl, alkoxy, alkoxymethyl or aralkyloxy;

$R_1$ and $R_2$ groups and $R_4$ and $R_5$ groups are also each independently linked together to form phenyl;

$R_1$ and $R_4$ are also each independently alkylene which is linked respectively to $R_2$ and $R_5$ to form benzocycloalkyl;

$R_6$ is hydrogen or alkyl;

$R_7$ is cycloalkyl, aralkyl, aryloxymethyl or alkoxymethyl;

$R_6$ and $R_7$ are also linked together to form, together with the nitrogen and carbon atoms to which $R_6$ and $R_7$ are respectively attached, heterocyclyl; and R" is hydrogen, alkyl, aralkyl, cycloalkyl lower alkyl or palmitoyl;

or a pharmaceutically acceptable salt thereof.

A preferred class of compounds of the present development which are useful in the practice of the invention include those described by formula (V) wherein:

R is higher alkylcarbonyl or multi-cycloalkyl carbonyl;

$R_1$ and $R_4$ are each independently hydrogen or lower alkyl;

$R_2$ and $R_5$ are each independently hydrogen, lower alkyl, phenyl, aryl lower alkyl, lower alkoxy, lower alkyloxymethyl or aryl lower alkyloxy;

$R_1$ and $R_2$ groups and $R_4$ and $R_5$ groups are also each independently linked together to form phenyl;

$R_1$ and $R_4$ are also each independently alkylene which is linked respectively to $R_2$ and $R_5$ to form benzocycloalkyl;

$R_6$ is hydrogen or lower alkyl;

$R_7$ is cycloalkyl, aryl lower alkyl, aryloxymethyl or lower alkoxymethyl;

$R_6$ and $R_7$ are also linked together to form, together with the nitrogen and carbon atoms to which $R_6$ and $R_7$ are respectively attached, heterocyclyl; and R" is hydrogen, lower alkyl, aryl lower alkyl, cycloalkylmethyl or palmitoyl.

A more preferred class of compounds of the present development include those of formula (V) wherein:

R is adamantoyl or palmitoyl;

$R_1$ and $R_4$ are each independently hydrogen or methyl;

$R_2$ and $R_5$ are each independently lower alkyl, lower alkoxy, phenyl, benzyl or benzyloxy;

$R_1$ and $R_2$ groups and $R_4$ and $R_5$ groups are also each independently linked together to form phenyl;

$R_1$ and $R_4$ are also each independently alkylene which is linked respectively to $R_2$ and $R_5$ to form indanyl;

$R_7$ is benzyl wherein the phenyl ring is optionally substituted with hydroxy;

$R_6$ and $R_7$ are also linked together to form, together with the nitrogen and carbon atoms to which $R_6$ and $R_7$ are respectively attached, saturated heterocyclyl of 5 or 6 members; and R" is hydrogen.

Compounds of the present development contain several asymmetric centers and may exist in the form of pure stereoisomers or in the form of mixtures of stereoisomers. The carbon atoms marked by an asterisk (*) designate asymmetric centers. In the compounds of the present development, unless stated otherwise, designations regarding the stereochemical configurations at the carbon atoms marked by an asterisk relate: sequentially starting from the carbon atom closest to the O-terminal side of the molecule, i.e., the amino acid residue. Preferred compounds of the present development include those wherein any of the carbon atoms marked by an asterisk (*) have the S configuration. Preferred also include the compounds of formula (IV) according to the development having a stereochemical designation selected from the group consisting of R,R,S, S,R,S, S,S,S and R,S,S, and more preferred compounds have a stereochemical designation of S,S,S or R,S,S. Preferred compounds of formula (V) are those wherein the carbon atoms of the principal chain marked by an asterisk (*) have the L configuration.

Subject Matter of the Development Which is Common to Each of the International Applications and to Each of the Aforementioned Classes of Compounds The following discussion is directed to subject matter that is common to all of the international applications and relates to each of the various classes of compounds which are useful for practice of the invention and which are described hereinbefore.

The compounds of the present invention may be useful in the form of the free base or acid or in the form of a pharmaceutically acceptable salt thereof. All forms are within the scope of the invention.

Where the compounds of the invention are substituted with an acidic moiety, base addition salts may be formed and are simply a more convenient form for use; in practice, use of the salt form inherently amounts to use of the free acid form. The bases which can be used to prepare the base addition salts preferably include those which produce, when combined with the free acid, pharmaceutically acceptable salts, that is, salts whose cations are non-toxic to the animal organism in pharmaceutical doses of the salts, so that the inhibition of NEP and/or ACE, and preferably beneficial mixed NEP and ACE inhibition (which is preferably inherent in the compounds of the invention), is not vitiated by side effects ascribable to the cations. Although pharmaceutically acceptable salts of said acidic compounds are preferred, all base addition salts are useful as sources of the free acid form even if the particular salt, per se, is desired only as an intermediate as, for example, when the salt is formed only for purposes of purification and/or identification, or when it is used as intermediate in preparing a pharmaceutically acceptable salt by ion exchange procedures. Pharmaceutically acceptable salts within the scope of the invention include those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, and is preferably an alcohol, such as methanol or ethanol, a ketone, such as acetone, an aliphatic ether, such as tetrahydrofuran, or an ester, such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols, such as methanol or ethanol, ethers, such as tetrahydrofuran, nitriles, such as acetonitrile, and ketones, such as acetone. Amino acid salts may be similarly prepared.

Preferred base addition salts have a cation selected from the group consisting of ammonium, sodium, calcium, protonated N-methyl-D-glucamine, protonated lysine, protonated arginine and protonated dicyclohexylamine.

Where the compounds of the present invention are substituted with a basic moiety, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the inhibition of NEP and/or ACE, and preferably beneficial mixed NEP and ACE inhibition (which is preferably inherent in the compounds of the invention), is not vitiated by side effects ascribable to the anions. Pharmaceutically acceptable salts within the scope of the invention are those derived from the following acids: mineral acids, such as hydrochloric acid, sulfuric acid, phosphoric acid and sulfamic acid; and organic acids, such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Compounds within the scope of the present invention, when administered to mammals, are potent ACE and/or NEP inhibitors. The present compounds are antihypertensives preferably due to double inhibitory action of both NEP and ACE.

The ACE inhibitors within the scope of the present invention are capable of blocking increases in blood pressure which are caused by increases in vascular resistance and the blood volume due to the formation of angiotensin II from angiotensin I. ACE inhibitors block the production of angiotensin II and, therefore, associated increases in blood pressure.

The NEP inhibitors within the scope of the present invention regulate auricular natriuretic peptide which is implicated in the regulation of arterial pressure. This peptide is liberated by the heart, possesses vasodilatory properties and is capable of controlling diuresis and natriuresis. Auricular natriuretic peptide is inactivated by NEP in the peripheral tissues. By inhibiting NEP with the compounds of the invention, a significant augmentation in diuresis and natriuresis in man is induced without causing an increase in the amounts of renin and aldosterone which is associated with diuretics that are generally used in association with ACE inhibitors.

Compounds of the invention that are mixed inhibitors of NEP and ACE may be used to alleviate hypertension of various origins without the co-administration of other diuretics.

Compounds according to the present invention are effective in the treatment of congestive heart failure and various types of hypertension, including hypertension which is associated with an increase in blood volume. Accordingly, the antihypertensive properties of the present compounds, and especially those which are inhibitors of both ACE and NEP, are preferred to the biological effects which are obtained with the concomitant administration of either, or both, of NEP and ACE inhibitors.

The enzymatic inhibitory properties of compounds according to the present invention are measured using [$^3$H]D-Ala$^2$-Leu-enkephalin as a substrate for neutral endopeptidase as described previously by Llorens et al., Biochem. Biophys. Res. Commun., 96, 1710 (1980) and Z-Phe-His-Leu in the case of peptidyldipeptidase A according to the process described in Biochem. Biophys. Acta, 206, 136–142 (1970).

The antihypertensive properties of the present compounds are determined in rat models including that of rat hypertension induced by DOCA salt and the spontaneously hypertensive male rat (SHR) according to Trapani et al., J. Cardiovasc. Pharmacol., 14, 419–424 (1989).

The products according to the invention may generally be administered orally or parenterally for the treatment of patients suffering from hypertension.

The products according to the invention, in base or salt form, may be presented in forms permitting administration by the most suitable route. Thus, the present invention relates also to pharmaceutical compositions, containing at least one product according to the invention, which are suitable for use in human or veterinary medicine. These compositions may be prepared according to customary methods, using one or more pharmaceutically acceptable adjuvants or excipients. The adjuvants comprise, inter alia, diluents, sterile aqueous media and various non-toxic organic solvents. The compositions may be presented in the form of tablets, pills, granules, powders, aqueous solutions or suspensions, injectable solutions, elixirs or syrups, and can contain one or more agents selected from sweeteners, flavorings, colorings, and stabilizers, to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients, such as lactose, sodium citrate, calcium carbonate and dicalcium phosphate, disintegrating agents, such as starch, alginic acids and certain complex silicates, combined with lubricants, such as magnesium stearate, sodium lauryl sulphate and talc, may be used for preparing tablets. To prepare a capsule, it is advantageous to use lactose and high molecular weight polyethylene glycols. Aqueous suspensions can contain emulsifying agents or agents which facilitate suspension. Diluents, such as ethanol, propylene glycol, glycerol and chloroform or mixtures thereof, may also be used.

For parenteral administration, suspensions or solutions of the products according to the invention in sesame oil, groundnut oil or olive oil, or aqueous solutions of propylene glycol, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the provisos that their pH is suitable adjusted, they are judiciously buffered and rendered isotonic with a sufficient quantity of glucose or sodium chloride, and they are sterilized by heating or microfiltration.

The doses of the present medicinal products used in the methods according to the invention are those which lead to a maximal therapeutic effect until an improvement is obtained. In general, the doses used are those which are therapeutically effective for lowering blood pressure during the treatment of hypertension. In general, the doses of product administered orally are between 0.1 and 100 mg/kg, and preferably between 1 and 10 mg/kg. The doses of product administered intravenously are between 0.01 and 10 mg/kg, and preferably between 0.1 and 5 mg/kg, on the understanding that, in each particular case, the doses will be determined in accordance with the factors distinctive to the subject to be treated, such as age, weight, general state of health and other characteristics which can influence the efficacy of the medicinal product.

The products according to the invention may be administered as frequently as necessary to obtain the desired therapeutic effect. Some patients may respond rapidly to a higher or lower dose and may find much weaker maintenance doses adequate. For other patients, it may be necessary to have long-term treatments at the rate of one to four doses per day, in accordance with the physiological requirements of each particular patient. Generally, the active product may be administered orally one to four times per day. It goes without saying that, for other patients, it will be necessary to prescribe not more than one or two doses per day.

The products according to the invention may be used in injectable form in emergency cases of acute hypertension. Such a treatment may be followed by an intravenous perfusion of the active product so as to obtain and maintain the desired therapeutic effect.

Methods for the Preparation of Compounds of the Invention

The following discussion relates to methods for the preparation of the various classes of compounds of the present invention.

Methods for the Preparation of Compounds Which are the Subject Also of International Application No. 1

In connection with the subject matter of the development which is the subject also of international application No. 1, compounds may be prepared by the acylation of a dipeptide of formula (VI)

with an acid of the formula

under conditions generally used in peptide chemistry and which are described, for example, by Bodansky et al., "Peptide Synthesis" J. Wiley & Sons, and wherein R, $R_1$, $R_2$, $R_4$, $R_5$, $R_6$, $R_7$ and R' are as described previously in connection with the subject matter of international application No. 1.

The acid reactant of formula (VII) may be prepared from the corresponding α-amino acid by halogenating deamination according to Fischer, Ann., 357, 1–24 (1907), followed by nucleophilic substitution of the halogen atom.

Embodiments of the present development are described in the following non-limiting examples which include pharmacological test procedures believed to correlate to therapeutic activity in humans and other animals.

Preparation of Intermediates of Compounds of the Development

EXAMPLE 1

(R)-2-Bromo-3-phenylpropanoic Acid

Sodium nitrite (27 g in water) is added at 0° C. to a solution of D-phenylalanine (40 g) in a mixture of 48% hydrobromic acid/water (1:1 by volume). The mixture is stirred for 30 minutes at 0° C. and then for 2 hours 30 minutes at a temperature close to 0° C. The reaction mixture is extracted with ether. The organic extracts are washed with water and a saturated sodium chloride solution and then dried over sodium sulphate. After filtration and concentration to dryness, the obtained residue is purified by distillation. (R)-2-Bromo-3-phenylpropanoic acid (33 g) is obtained which has the following characteristics: $B.p._{1kPa}=154°$ C.; $R_f=0.47$ (methylene chloride/methanol). The yield is 60%.

EXAMPLE 2

(S)-2-Acetylthio-3-Phenlylpropanoic Acid

Thioacetic acid (9.3 cc) and potassium carbonate (7.5 g) in water (150 cc) are added under nitrogen atmosphere to a solution of (R)-2-bromo-3-phenylpropanoic acid (25 g) in 1M sodium hydroxide (110 cc). The solution is stirred for 15 hours at a temperature close to 20° C. After evaporation under reduced pressure, the residue is taken up with water and ethyl acetate. The aqueous phase is separated, acidified to pH=2 and then extracted with ethyl acetate. After washing, the organic phase is dried over sodium sulphate. After filtration and concentration under reduced pressure, (S)-2-acetylthio-3-phenylpropanoic acid (18.5 g) is obtained with a yield of 75% in the form of an oil having the following characteristics: $R_f=0.49$ [hexane/ethyl acetate/acetic acid (6:4:0.5 by volume)].

EXAMPLE 3

(R)-2-Bromo-3-Phenylpentanoic Acid

Working as in Example 1, but starting from D-isoleucine, (R)-2-bromo-3-phenylpentanoic acid having the following characteristics is obtained with a yield of 74%: $R_f=0.38$ [methylene chloride/methanol (1:1 by volume)].

EXAMPLE 4

(S)-2-Acetylthio-3-Phenylpentanoic Acid

A solution of (R)-2-bromo-3-phenylpentanoic acid in dimethylformamide is added to a solution of thioacetic acid (1.5 equivalents) and sodium hydride (2.5 equivalents) in anhydrous dimethylformamide. The mixture is stirred for 3 hours at a temperature close to 20° C. After customary treatment, (S)-2-acetylthio-3-phenylpentanoic acid is obtained with a yield of 78% in the form of a yellow oil having the following characteristics: $R_f=0.44$ [methylene chloride/methanol (9:1 by volume)].

EXAMPLE 6

(R)-2-Bromo-4-Phenylbutanoic Acid

Working as in Example 1, but starting from D-2-amino-4-phenylbutanoic acid, (R)-2-bromo-4-phenylbutanoic acid having the following characteristics is obtained with a yield of 72%: $R_f=0.30$ [methylene chloride/methanol/acetic acid (10:0.1:0.2 by volume)].

EXAMPLE 6

(S)-2-Acetylthio-4-Phenylbutanoic Acid

Working as in Example 4 but starting from (R)-2-bromo-4-phenylbutanoic acid, (S)-2-acetylthio-4-phenylbutanoic acid having the following characteristics is obtained with a yield of 80%: $R_f=0.35$ [methylene chloride/methanol/acetic acid (9:0.3:0.1 by volume)].

EXAMPLE 7

(R)-2-Bromo-3-Methylbutanoic Acid

Working as in Example 1, but starting from D-valine, (R)-2-bromo-3-methylbutanoic acid is obtained with a yield of 69% in the form of an oil which crystallizes slowly having the following characteristics: $R_f=0.52$ [methylene chloride/methanol/acetic acid (3:0.5:0.5 by volume)].

EXAMPLE 8

(S)-2-Acetylthio-3-Methylbutanoic Acid

Working as in Example 2, but starting from (R)-2-bromo-3-methylbutanoic acid, (S)-2-acetylthio-3-methylbutanoic acid is obtained with a yield of 94% in the form of an oil having the following characteristics: $R_f=0.28$ [n-hexane/ethyl acetate (4:6 by volume)].

EXAMPLE 9

(R)-2-Bromo-2-Phenylacetic Acid

Working as in Example 1, but starting from D-phenylglycine, (R)-2-bromo-2-phenylacetic acid is obtained with a yield of 72% in the form of an oil which crystallizes slowly having the following characteristics: $R_f=0.63$ [methylene chloride/methanol/acetic acid (9:1:0.5 by volume)].

EXAMPLE 10

(S)-2-Acetylthio-2-Phenylacetic Acid

Working as in Example 2, but starting from (R)-2-bromo-2-phenylacetic acid, (S)-2-acetylthio-2-phenylacetic acid is obtained with a yield of 74% in the form of an oil which crystallizes slowly having the following characteristics: $R_f=0.42$ [n-hexane/ethyl acetate (4:6 by volume)].

EXAMPLE 11

L-Ile-Tyr-OMe (A) A solution of methyl tyrosinate hydrochloride (1 equivalent) and triethylamine (1 equivalent) in chloroform, a solution of hydroxybenzotriazole (1 equivalent) in tetrahydrofuran, and a solution of dicyclohexylcarbodiimide in chloroform are added successively at 0° C. to a solution of t-butoxycarbonyl-L-isoleucine in tetrahydrofuran. The mixture is stirred for 1 hour at 0° C. and then for 16 hours at a temperature close to 20° C. After customary treatment, the protected dipeptide (Boc-L-Ile-Tyr-OMe) having the following characteristics is obtained with a yield of 98%: $R_f=0.47$ [methylene chloride/methanol (9:1 by volume)].

(B) The protected dipeptide is dissolved in methylene chloride and then treated with 20 equivalents of trifluoroacetic acid. After 1 hour at 0° C. and 2 hours at a temperature close to 20° C., the mixture is concentrated under reduced pressure. The residue is triturated with ether and then dried under reduced pressure. The dipeptide L-Ile-Tyr-OMe is thus obtained with a yield of 98% in the form of a white solid having the following characteristics: $R_f=0.23$ [methylene chloride/methanol (9:1 by volume)].

EXAMPLE 12

L-Val-Tyr-OMe (A) Working as in Example 11(A), but starting from t-butoxycarbonyl-L-valine and methyl tyrosinate hydrochloride, the protected dipeptide (Boc-L-Val-Tyr-OMe) is obtained with a yield of 98% in the form of an oil having the following characteristics: $R_f=0.53$ [methylene chloride/methanol (9:1 by volume)].

(B) The elimination of the protective group is carried out under the conditions described in Example 11(B). The dipeptide L-Val-Tyr-OMe is thus obtained with a yield of 98% in the form of a white solid having the following characteristics: $R_f=0.40$ [methylene chloride/methanol/acetic acid (8:2:0.5 by volume)].

EXAMPLE 13

L-Nle-Tyr-OMe (A) Working as in Example 11(A), but starting from t-butoxycarbonyl-L-norleucine and methyl tyrosinate hydrochloride, the protected dipeptide Boc-L-Nle-Tyr-OMe is obtained with a yield of 99% in the form of an oil having the following characteristics: $R_f=0.67$ [methylene chloride/methanol (9:1 by volume)].

(B) The elimination of the protective group is carried out under the conditions described in Example 11(B). The dipeptide L-Nle-Tyr-OMe is thus obtained with a yield of 70% in the form of a white solid having the following characteristics: $R_f=0.10$ [methylene chloride/methanol (25:5 by volume)].

EXAMPLE 14

L-Leu-Tyr-OMe (A) Working as in Example 11(A), but starting from t-butoxycarbonyl-L-leucine and methyl tyrosinate hydrochloride, the protected dipeptide Boc-L-Leu-Tyr-OMe is obtained with a yield of 99% in the form of an oil having the following characteristics: $R_f=0.42$ [methylene chloride/methanol (9:1 by volume)].

(B) The elimination of the protective group is carried out under the conditions described in Example 11(B). The dipeptide L-Leu-Tyr-OMe is thus obtained with a yield of 82% in the form of a white solid having the following characteristics: $R_f=0.11$ [methylene chloride/methanol (9:1 by volume)].

EXAMPLE 15

L-Phe-L-Tyr-OMe (A) Working as in Example 11(A), but starting from t-butoxycarbonyl-L-phenylalanine and methyl L-tyrosinate hydrochloride, the protected dipeptide Boc-L-Phe-L-Tyr-OMe is obtained with a yield of 97% in the form of an oil having the following characteristics: $R_f=0.5$ [methylene chloride/methanol (9:1 by volume)].

(B) The elimination of the protective group is carried out under the conditions described in Example 11(B). The dipeptide L-Phe-L-Tyr-OMe is thus obtained with a yield of 85% in the form of a white solid having the following characteristics: $R_f=0.25$ [methylene chloride/methanol/acetic acid (9:1:0.5 by volume)].

EXAMPLE 16

L-Ile-L-Pro-OMe (A) Working as in Example 11(A), but starting from t-butoxycarbonyl-L-isoleucine and methyl L-prolinate, the protected dipeptide Boc-L-Ile-L-Pro-OMe is obtained with a yield of 92% in the form of an oil having the following characteristics: $R_f=0.44$ [methylene chloride/methanol (9:0.5 by volume)].

(B) The elimination of the protective group is carried out under the conditions described in Example 11(B). The dipeptide L-Ile-L-Pro-OMe is thus obtained with a yield of 96% in the form of a white solid having the following characteristics: $R_f=0.37$ [methylene chloride/methanol/acetic acid (9:1:0.5 by volume)].

EXAMPLE 17

L-Val-L-Pro-OMe (A) Working as in Example 11(A), but starting from t-butoxycarbonyl-L-valine and methyl L-prolinate, the protected dipeptide Boc-L-Val-L-Pro-OMe is obtained with a yield of 98% in the form of an oil having the following characteristics: $R_f=0.42$ [methylene chloride/methanol (9:0.5 by volume)].

(B) The elimination of the protective group is carried out under the conditions described in Example 11(B). The dipeptide L-Val-L-Pro-OMe is thus obtained with a yield of 86% in the form of a white solid having the following characteristics: $R_f=0.50$ [methylene chloride/methanol/acetic acid (9:1:0.5 by volume)].

EXAMPLE 18

L-Ile-L-Pip-OMe (A) Working as in Example 11(A), but starting from t-butoxycarbonyl-L-isoleucine and L-2-methoxycarbonylpiperidine, the protected dipeptide Boc-L-Ile-L-Pip-OMe is obtained with a yield of 89% in the form of an oil having the following characteristics: $R_f=0.70$ [methylene chloride/methanol/acetic acid (9:1:0.5 by volume)].

(B) The elimination of the protective group is carried out under the conditions described in Example 11(B). The dipeptide L-Ile-L-Pip-OMe is thus obtained with a yield of 79% in the form of a white solid having the following characteristics: $R_f=0.42$ [methylene chloride/methanol/acetic acid (9:1:0.5 by volume)].

Preparation of Compounds of the Development

EXAMPLE 19

N-(2-Mercapto-3-phenylpropanoyl)-Val-Tyr

Val-Tyr-OMe trifluoroacetate (1 equivalent) and triethylamine (1 equivalent) in chloroform, a solution of 1-hydroxybenzotriazole (1 equivalent) in tetrahydrofuran and a solution of dicyclohexylcarbodiimide (1 equivalent) in chloroform are added successively at 0° C. to a solution of 2-acetylthio-3-phenylpropanoic acid (1 equivalent) in tetrahydrofuran. The mixture is stirred for 1 hour at 0° C. and for 16 hours at a temperature close to 20° C. The precipitate is separated by filtration and the filtrate is concentrated to dryness under reduced pressure. The residue obtained is dissolved in ethyl acetate and then washed successively with a 10% citric acid (w/v), water, 10% sodium carbonate (w/v), water, and saturated sodium chloride. The organic phase is dried over sodium sulphate. After filtration and concentration to dryness, the residue is purified by chromatography. N-(2-Acetylthio-3-phenylpropanoyl)-Val-Tyr-OMe is thus obtained with a yield of 70%, in the form of an oil. $R_f=0.54$ [methylene chloride/methanol (9:0.5 by volume)].

The purified oil prepared above is dissolved in degassed methanol and a 1M sodium hydroxide solution (3 equivalents) is added at 0° C. The mixture is stirred for 2 hours at a temperature close to 20° C. and then a partition is carried out between degassed water and degassed ethyl acetate. The aqueous phase is acidified to pH=2 and is then extracted with degassed ethyl acetate. The organic phase is washed with a saturated aqueous solution of sodium chloride, dried over sodium sulphate, filtered and then concentrated under reduced pressure. The residue obtained is chromatographed on silica gel, eluting with a methylene chloride/methanol/acetic acid mixture (9:0.5:0.5 by volume). N-(2-mercapto-3-phenylpropanoyl)-Val-Tyr is thus obtained with a yield of 65% in the form of a white solid having the following characteristics: high performance liquid chromatography: retention time: 8 minutes [acetonitrile/0.05% trifluoroacetic acid (45:55 by volume)]; proton nuclear magnetic resonance spectrum (deuterated dimethyl sulphoxide; chemical shifts in ppm): 0.8 [$CH_3$ (Val)]; 1.90 [CHβ(Val)]; 2.60 (HS); 2.70, 2.80 and 2.05 [$CH_2$β(Tyr+Phe)]; 3.70 [CHα(Val)]; 4.20 (CHα(Phe+Tyr)]; 6.6 and 6.95 [Ar(Tyr)]; 7.8 [Ar(Phe)]; 8.05 and 8.20 (NH); 9.15 [OH(Tyr)]; 12.45 (COOH).

EXAMPLE 20

N-(2-Mercapto-3-phenylpropanoyl)-Ile-Tyr-OMe

The coupling of 2-acetylthio-3-phenylpropanoic acid with the protected dipeptide Ile-Tyr-OMe is carried out under the conditions described in Example 19. N-(2-Acetylthio-3-phenylpropanoyl)-Ile-Tyr-OMe is obtained with a yield of 75% in the form of an oil. $R_f=0.17$ [hexane/ethyl acetate (5:5 by volume)].

Deprotection is carried out under the conditions of Example 19. N-(2-Mercapto-3-phenylpropanoyl)-Ile-Tyr-OMe is thus obtained with a yield of 70% in the form of a white solid melting at 185° C. $R_f=0.28$ [methylene chloride/methanol/acetic acid (9: 1:0.5 by volume)]; proton nuclear magnetic resonance spectrum (deuterated dimethyl sulphoxide; chemical shifts in ppm): 0.75 [$CH_3$(Ile)]; 1.1, 1.5 and 1.7 [CHβ$CH_2$γ(Ile)]; 2.70 (HS); 2.80, 2.90 and 3.15 [$CH_2$β(Phe+Tyr)]; 3.65, 4.15 and 4.30 [$CH_2$α(Phe+Ile+Tyr)]; 6.60 and 7.00 [Ar(Tyr)]; 7.20 [Ar(Phe)]; 8.00 and 8.20 (NH); 12.20 (COOH).

EXAMPLE 21

N-(2-Mercapto-3-phenylpropanoyl)-Ile-Pip

The coupling of 2-acetylthio-3-phenylpropanoic acid with the protected dipeptide Ile-Pip-OMe is carried out under the conditions described in Example 19. N-(2-Mercapto-3-phenylpropanoyl)-Ile-Pip-OMe is obtained with a yield of 51% in the form of an oil. $R_f=0.30$ [cyclohexane/ethyl acetate (5:5 by volume)].

Deprotection is carried out under the conditions described in Example 19. N-(2-Mercapto-3-phenylpropanoyl)-lie-Pip is thus obtained with a yield of 65% in the form of a white solid. $R_f=0.48$ [methylene chloride/methanol/acetic acid (9: 0.5: 0.25 by volume)]; proton nuclear magnetic resonance spectrum (deuterated dimethyl sulphoxide; chemical shifts in ppm): 0.80 [$CH_3$(Ile)]; 1.02, 1.50 and 2.05 [$CH_2$β, γand γ(Pip)]; 2.6 (HS); 2.80 and 3.05 [$CH_2$β(Phe)]; 3.7 [$CH_2$ε(Pip)]; 4.20, 4.70 and 4.95 (CHα; 7.20 [Ar(Phe)]; 8.20 and 8.40 (NH); 12.78 (COOH).

EXAMPLE 22

N-(2-Mercapto-3-phenylpropanoyl)-Nle-Tyr

The coupling of 2-acetylthio-3-phenylpropanoic acid with the protected dipeptide Nle-Tyr-OMe is carried out under the conditions described in Example 19. N-(2-Acetylthio-3-phenylpropanoyl)-Nle-Tyr-OMe is thus obtained with a yield of 64% in the form of an oil. $R_f=0.21$ [hexane/ethyl acetate (6:4 by volume)].

Deprotection is carried out under the conditions described in Example 19. N-(2-Mercapto-3-phenylpropanoyl)-Nle-Tyr is thus obtained with a yield of 61% in the form of a white solid. $R_f=0.53$ [methylene chloride/methanol (9:1 by volume)]; proton nuclear magnetic resonance spectrum (deuterated dimethyl sulphoxide; chemical shifts in ppm): 0.80 [$CH_3$(Nle)]; 1.25 and 1.50 [$CH_2$β, γ and δ(Nle)]; 2.00 (HS); 2.75 and 2.95 [$CH_2$β(Phe+Tyr)]; 3.70 and 4.20 [CHα(Nle, Phe, Tyr)]; 6.60 and 6.95 [Ar(Tyr)]; 7.20 [Ar(Phe)]; 8.10 and 8.20 (NH); 9.15 [OH(Tyr)]; 12.3 (COOH); high performance liquid chromatography: retention time: 9.3 minutes [acetonitrile/0.05% trifluoroacetic acid (46:54 by volume)].

EXAMPLE 23

N-(2-Mercapto-3-phenylpropanoyl)-Leu-Tyr

The coupling of 2-acetylthio-3-phenylpropanoic acid with the protected dipeptide Leu-Tyr-OMe is carried out under the conditions described in Example 19. N-(2-Acetylthio-3-phenylpropanoyl)-Leu-Tyr-OMe is thus obtained in the form of an oil. $R_f=0.18$ [cyclohexane/ethyl acetate (5:5 by volume)].

Deprotection is carried out under the conditions described in Example 19. N-(2-Mercapto-3-phenylpropionyl)-Leu-Tyr is thus obtained with a yield of 70% in the form of a white solid. $R_f=0.45$ [methylene chloride/methanol/acetic acid (9:1:0.5 by volume)]; proton nuclear magnetic resonance spectrum (deuterated dimethyl sulphoxide; chemical shifts in ppm): 0.80 [$CH_3$ (Leu)]; 1.30 [$CH_2$β(Leu)]; 1.5 ($CH_2$γ(Leu)]; 2.60 (HS); 2.70, 2.80 and 3.00 [$CH_2$β(Phe+Tyr)]; 3.50 and 4.20 [$CH_2$α(Phe, Leu, Tyr)]; 6.60 and 6.90 [Ar(Tyr)]; 7.20 [Ar(Phe)]; 7.90 and 8.05 (NH); 9.10 [OH(Tyr)]; 9.10 [OH(Tyr)]; 12.50 (COOH).

EXAMPLE 24

N-(2-Mercapto-3-methylpentanoyl)-Phe-Tyr

The coupling of 2-acetylthio-3-methylpentanoic acid with the protected dipeptide Phe-Tyr-OMe is carried out under the conditions described in Example 19. N-(2-Acetylthio-3-methylpentanoyl)-Phe-Tyr-OMe is thus obtained with a yield of 78% in the form of an oil. $R_f$=0.14 [cyclohexane/ethyl acetate (6:4 by volume)].

Deprotection is carried out under the conditions described in Example 19. N-(2-Mercapto-3-methylpentanoyl)-Phe-Tyr melting at 120° C. is thus obtained with a yield of 70%. $R_f$=0.40 [methylene chloride/methanol/acetic acid (9:1:0.2 by volume)]; proton nuclear magnetic resonance spectrum (deuterated dimethyl sulphoxide; chemical shifts in ppm): 0.75 [$CH_3$(Ile)]; 1.00, 1.20 and 1.60 [$CH_2\beta$, $CH_2\gamma$(Ile)]; 2.65 (HS); 2.70 and 2.90 [$CH_2\beta$(Phe+Tyr)]; 6.60 and 6.95 [Ar(Tyr)]; 7.13 [Ar(Phe)]; 8.00 and 8.05 (NH); 9.10 [OH(Tyr)]; 12.6 (COOH).

EXAMPLE 25

N-(2-Mercapto-3-methylpentanoyl)-Val-Tyr

The coupling of 2-acetylthio-3-methylpentanoic acid with the protected dipeptide Val-Tyr-OMe is carried out under the conditions described in Example 19. N-(2-Acetylthio-3-methylpentanoyl)-Val-Tyr-OMe is thus obtained with a yield of 78% in the form of an oil. $R_f$=0.41 [methylene chloride/methanol/acetic acid (9:5:0.5 by volume)].

Deprotection is carried out under the conditions described in Example 19. N-(2-Mercapto-3-methylpentanoyl)-Val-Tyr is thus obtained with a yield of 72% in the form of a white solid melting at 150° C. $R_f$=0.20 [methylene chloride/methanol/acetic acid (9:0.5:0.25 by volume)]; proton nuclear magnetic resonance spectrum (deuterated dimethyl sulphoxide; chemical shifts in ppm): 0.80 [$CH_3$(Val +Ile)]; 1.00 and 1.25 [$CH_2\gamma$(Ile)]; 1.65 [$CH\beta$(Ile)]; 1.90 [$CH\beta$(Val)]; 2.30 (HS); 2.70 and 2.85 [$CH_2\beta$(Tyr)]; 3.30 [$CH\alpha$(Ile)]; 4.20 and 4.32 [$CH\alpha$(Val and Tyr)]; 6.68 and 6.95 [Ar (Tyr)]; 7.90 and 8.10 [NH(Val and Tyr)]; 9.20 [OH(Tyr)]; 12.56 (COOH).

EXAMPLE 26

N-(2-Mercapto-4-phenylbutanoyl)-Val-Tyr

The coupling of 2-acetylthio-4-phenylbutanoic acid with the protected dipeptide Val-Tyr-$OCH_3$ is carried out under the conditions described in Example 19. N-(2-Acetylthio-4-phenylbutanoyl)-Val-Tyr-$OCH_3$ is thus obtained with a yield of 82% in the form of an oil. $R_f$=0.49 [cyclohexane/ethyl acetate (5:5 by volume)].

Deprotection is carried out under the conditions described in Example 19. N-(2-Mercapto-4-phenylbutanoyl)-Val-Tyr is thus obtained with a yield of 98% in the form of a white solid melting at 105° C. $R_f$=0.65 [methylene chloride/methanol/acetic acid (9:1:0.5 by volume)]; high performance liquid chromatography: retention time: 9.10 minutes [acetonitrile/0.05% trifluoroacetic acid (45:55 by volume)]; proton nuclear magnetic resonance spectrum (deuterated dimethyl sulphoxide; chemical shifts in ppm): 0.75 [$CH_3$(Val)]; 1.75 [$CH\beta$(Val)]; 1.95 [$CH_2\gamma$(Phe)]; 2.50 [$CH_2\beta$(Phe)]; 2.72 and 2.90 [$CH_2\beta$(Tyr)]; 3.45 [$CH\alpha$(Phe)]; 4.20 and 4.30 [$CH\alpha$(Tyr and Val)]; 6.60 and 7.00 [Ar(Tyr)]; 7.12 and 7.20 [Ar(Phe)]; 7.20 and 8.10 (NH); 9.15 [OH(Tyr)]; 12.35 (COOH).

EXAMPLE 27

N-(2-Mercapto-3-methylbutanoyl)-Ile-Tyr

The coupling of (S)-2-acetylthio-3-methylbutanoic acid with the protected dipeptide Ile-Tyr-$OCH_3$ is carried out under the conditions described in Example 19. N-(2-Acetylthio-3-methylbutanoyl)-Ile-Tyr-$OCH_3$ is obtained with a yield of 85% in the form of an oil. $R_f$=0.28 [n-hexane/ethyl acetate (4:6 by volume)].

Deprotection is carried out under the conditions described in Example 19. N-(2-Mercapto-3-methylbutanoyl)-Ile-Tyr is obtained with a yield of 89% in the form of a white solid melting at 199° C. $R_f$=0.42 [methylene chloride/methanol/acetic acid (9:1:0.5 by volume)]; proton nuclear magnetic resonance spectrum (deuterated dimethyl sulphoxide; chemical shifts in ppm): 0.75 and 0.90 [$CH_3$(Val and Ile)]; 1 [$CH\beta$(Ile)]; 1.40 and 1.65 [$CH_2\gamma$(Ile)]; 1.80 [$CH\beta$(Val)]; 2.30 (HS); 2.75 and 2.89 [$CH_2\beta$(Tyr)]; 3.15 [CH(SH)]; 4.15 [$CH\alpha$(Ile)]; 4.32 [$CH\alpha$(Tyr)]; 6.55 and 6.95 [Ar(Tyr)]; 7.9 and 8.10 (NH); 9.12 [OH (Tyr)]; 12.10 (COOH); high performance liquid chromatography: retention time: 5.84 minutes [acetonitrile/0.05% trifluoroacetic acid (5:5 by volume)].

EXAMPLE 28

N-(2-Mercapto-2-phenylacetyl)-Ile-Tyr

The coupling of (S)-2-acetylthio-2-phenylacetic acid with the protected dipeptide Ile-Tyr-$OCH_3$ is carried out under the conditions described in Example 19. N-(2-Acetylthio-2-phenylacetyl)-Ile-Tyr-$OCH_3$ is obtained with a yield of 46% in the form of an oil. $R_f$=0.42 [n-hexane/ethyl acetate (4:6 by volume)].

Deprotection is carried out under the conditions described in Example 19. N-(2-Mercapto-2-phenylacetyl)-Ile-Tyr is obtained with a yield of 73% in the form of an oil. $R_f$=0.42 [methylene chloride/methanol/acetic acid (9:1:0.5 by volume)]; proton nuclear magnetic resonance spectrum (deuterated dimethyl sulphoxide; chemical shifts in ppm): 0.61 and 0.72 [$CH_3$(Ile)]; 1.1 [$CH\beta$(Ile)]; 1.4 and 1.7 [$CH_2\gamma$(Ile)]; 2.32 (HS); centered on 2.80 [$CH_2\beta$(Tyr)]; 3.3 [CH(SH)]; 4.20 [$CH_2\alpha$(Tyr)]; 4.82 [$CH\alpha$(Ile)]; 6.55 and 6.95 [Ar(Tyr)]; centered on 7.30 [Ar(Phe)]; 8.15 [NH(Ile and Tyr)]; 9.10 [OH(Tyr)]; 12.45 (COOH).

EXAMPLES 29 to 53

Working as in Example 19, compounds of formula (III) and which are set forth in Table II are prepared.

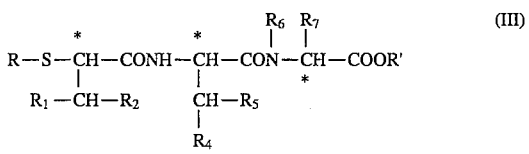

TABLE II

| Example | R₁ | R₂ | R₄ | R₅ | R₆ | R₇ |
|---|---|---|---|---|---|---|
| 29 | CH₃ | CH₂CH₃ | CH₃ | CH₂CH₃ | H | CH₂—C₆H₄—OH |
| 30 | CH₃ | CH₂CH₃ | CH₃ | OCH₃ | H | CH₂—C₆H₄—OH |
| 31 | CH₃ | CH₂CH₃ | CH₃ | OCH₃ | | cyclopentyl |
| 32 | CH₃ | CH₂CH₃ | CH₃ | OCH₃ | | 1-hydroxycyclopentyl |
| 33 | CH₃ | CH₂CH₃ | CH₃ | OCH₂—C₆H₅ | H | CH₂—C₆H₄—OH |
| 34 | CH₃ | CH₃ | CH₃ | CH₃ | H | CH₂—C₆H₄—OH |
| 35 | CH₃ | CH₃ | CH₃ | OCH₃ | H | CH₂—C₆H₄—OH |
| 36 | CH₃ | CH₃ | CH₃ | OCH₂—C₆H₅ | H | CH₂—C₆H₄—OH |
| 37 | CH₃ | CH₃ | CH₃ | OCH₂—C₆H₅ | | cyclopentyl |
| 38 | CH₃ | OCH₃ | CH₃ | CH₂CH₃ | H | CH₂—C₆H₄—OH |
| 39 | CH₃ | OCH₃ | CH₃ | C₆H₅ | H | CH₂—C₆H₄—OH |
| 40 | CH₃ | OCH₃ | | indanyl | H | CH₂—C₆H₄—OH |
| 41 | CH₃ | OCH₂—C₆H₅ | | CH₃ | CH₂CH₃  H | CH₂—C₆H₄—OH |
| 42 | C₆H₅ | | CH₃ | CH₃ | | cyclopentyl |

TABLE II-continued

| Example | $R_1$ | $R_2$ | $R_4$ | $R_5$ | $R_6$ | $R_7$ |
|---|---|---|---|---|---|---|
| 43 | 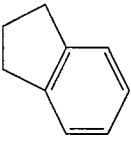 | | $CH_3$ | $CH_2CH_3$ | H | 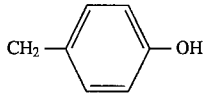 |
| 44 | $CH_3$ | $CH_2CH_3$ |  | | H | 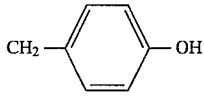 |
| 45 | $CH_3$ | $CH_3$ |  | | H |  |
| 46 | $CH_3$ | $CH_3$ |  | | |  |
| 47 | $CH_3$ | $CH_2CH_3$ |  | | H | 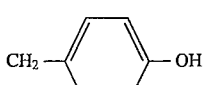 |
| 48 | $CH_3$ | $CH_2CH_3$ | H | H | |  |
| 49 | $CH_3$ | $CH_2CH_3$ |  | | |  |
| 50 |  | |  | | H | 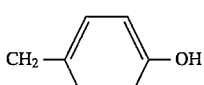 |
| 51 |  | | $CH_3$ | $CH_3$ | H | 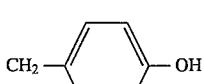 |
| 52 |  | | $CH_3$ |  | H | 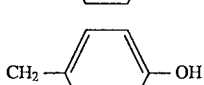 |
| 53 |  | | $CH_3$ | $OCH_2CH_3$ | H |  |

Selected pharmacological data for certain preferred compounds of the present development are presented in Table III below.

TABLE III

| | Inhibitory Effect on NEP and ACE | |
|---|---|---|
| Examples | $IC_{50}$ (nM) NEP | $IC_{50}$ (nM) ACE |
| 19 | 5 ± 2 | 4 ± 1 |
| 20 | 3.2 ± 0.3 | 2.5 ± 0.1 |
| 21 | 5 ± 2 | 2 ± 1 |
| 22 | 18 ± 2 | 30 ± 5 |
| 23 | 3 ± 2 | 30 ± 5 |
| 24 | 3 ± 1 | 8 ± 2 |
| 25 | 5 ± 2 | 2 ± 0.5 |
| 26 | 10 ± 1 | 8 ± 2 |
| 27 | 1.4 ± 0.2 | 0.3 ± 0.1 |
| 28 | 4.5 ± 0.5 | 3.5 ± 0.5 |

Methods for the Preparation of Compounds Which are the Subject Also of International Application No. 2

Throughout the discussion which follows and which is directed to methods for the preparation of compounds that are the subject also of international application No. 2, R, $R_1$, $R_2$, $R_3$ and R' are as described previously in connection with the discussion involving international application No. 2.

Compounds of the invention which are the subject also of international application No. 2 may be prepared by the acylation of an amino acid of formula (VIII)

$$H_2N-\overset{*}{\underset{R_3}{CH}}-COOR' \qquad (VIII)$$

with an acid of formula (IX)

$$R-S-CH_2-\overset{*}{\underset{R_1-CH-R_2}{CH}}-COOH \qquad (IX)$$

under conditions generally used in peptide chemistry and which are described, for example, by Bodansky et al., "Peptide Synthesis" J. Wiley & Sons Preferably, the acylation is conducted in the presence of a condensing agent, for example, dicyclohexylcarbodiimide, and optionally in the presence of 1-hydroxybenzotriazole.

The acid of formula (IX) may be obtained by the Michael addition of a sulfur derivative of formula (X)

$$R-SH \qquad (X)$$

to an acrylic acid of the formula (XI)

$$H_2C=\underset{R_1-CH-R_2}{C}-COOH \qquad (XI)$$

Preferably, thioacetic acid or thiobenzoic acid is used as a sulphur derivative of formula (X).

The acrylic acid of formula (XI) may be obtained by saponification of the corresponding ester in a basic medium. Preferably, the methyl or ethyl ester is used.

The acrylic ester of formula (XII)

$$H_2C=\underset{R_1-CH-R_2}{C}-COOR_8 \qquad (XII)$$

wherein $R_8$ preferably represents an alkyl radical containing 1 to 4 carbon atoms, may be obtained by a Mannich reaction on the monoester of formula (XIII)

$$R_8OCO-\overset{*}{\underset{R_1-CH-R_2}{CH}}-COOH \qquad (XIII)$$

wherein $R_8$ is as described previously.

Generally, the Mannich reaction is performed by means of formaldehyde in the presence of a secondary amine, such as diethylamine, at a temperature of about 20° C.

The monoester of formula (XIII) is obtained by monosaponification in a basic medium of a malonic ester of formula (XIV)

$$(R_8OCO)_2-\underset{R_1-CH-R_2}{CH} \qquad (XIV)$$

wherein $R_8$ is as described previously.

The malonic ester of formula (XIV) may be obtained by the action of a halide of formula (XV)

$$halo-\underset{R_2}{\overset{CH-R_1}{|}} \qquad (XV)$$

wherein halo is preferably bromine, on an alkyl malonate anionized previously, for example, by means of an alkali metal alcoholate which is optionally prepared in situ. The malonic ester of formula (XIV) may also be obtained by condensation of a ketone of formula (XVI)

$$O=\underset{R_2}{\overset{C-R_1}{|}} \qquad (XVI)$$

with an alkyl malonate anionized previously as described above, to form the compound of formula (XVII)

$$R_1-\underset{R_2\ COOR_8}{C=C}-COOR_8 \qquad (XVII)$$

wherein $R_8$ is as described previously, which is reduced catalytically, for example, with hydrogen in the presence of palladium on charcoal, to the malonic ester of formula (XIV).

The acrylic ester of formula (XII) may also be obtained by a Wittig reaction with formaldehyde on a phosphonate of formula (XVIII)

$$(R_8O)_2\overset{O}{\overset{\|}{P}}-\underset{R_1-CH-R_2}{CH}-COOR_8 \qquad (XVIII)$$

wherein $R_8$ is as defined above.

The compound of formula (XVIII) may be obtained by the action of a compound of formula (XV) on an alkyl phosphonoacetate of formula (XIX)

$$(R_8O)_2\overset{O}{\overset{\|}{P}}-CH_2COOR_8 \qquad (XIX)$$

wherein $R_8$ is defined as above.

The reaction is generally performed in the presence of a strong base, such as sodium hydride.

The N-(mercaptoacyl)amino acid compounds of formula (IV) in which R and R' each represent hydrogen may be obtained from the corresponding compound in which R and R' are other than hydrogen. For example, when R is acyl and R' is alkyl or phenylalkyl, their replacement by a hydrogen atom is generally performed by hydrolysis in an alkaline medium, working in an inert medium so as to avoid oxidation of the mercapto group.

The resolved forms of the compounds according to the invention may be prepared by standard practices known to those skilled in the art, including fractional crystallization and column chromatography. For example, compounds of formula (IX), for example, an acylthioalkanoic acid, may be resolved by fractional recrystallization with optically active bases such as methylbenzylamine and 1-(1-naphthyl)ethylamine. The resolved compounds of formula (IX) may then be reacted with an optically active amino acid according to the acylation reaction described above to yield compounds of formula (IV).

Embodiments of the present development are described in the following non-limiting examples which include pharmacological test procedures believed to correlate to therapeutic activity in humans and other animals.

Preparation of Intermediates of Compounds of the Development

EXAMPLE 54

2-Acetylthiomethyl-3-phenylbutanoic Acid

Ethyl malonate (4.1 mL) is added to a solution of sodium ethoxide prepared from sodium metal (0.75 g) and ethanol (40 mL). 1-Bromo-1-phenylethane (6 g) is added at 0° C.

and the mixture is then stirred for 20 hours at 30° C. After concentrating to dryness, the residue is taken up with water (100 mL) and then extracted three times with ethyl acetate (75 mL). The organic phase is washed with water and saturated sodium chloride solution and dried over magnesium sulphate. After filtering and concentrating to dryness, ethyl (1-phenylethyl)malonate (6 g) is obtained in an 84% yield in the form of a pale yellow oil, having the following characteristics: $R_f$=0.67 [hexane/ethyl acetate (65:35 by volume)].

The ethyl (1-phenylethyl)malonate is stirred overnight with sodium hydroxide (1.3 eq) in an acetone/water (3:1 by volume) mixture. After concentrating to dryness, the residue is taken up with water (40 mL) and the mixture is then extracted three times with ethyl acetate (25 mL). The organic phase is washed, dried, filtered and concentrated to dryness to yield 3.5 g of 2-ethoxycarbonyl-3-phenylbutanoic acid in a 65% yield in the form of an oil, having the following characteristics: $R_f$=0.50 [methylene chloride/methanol (9:1 by volume)].

To the 2-ethoxycarbonyl-3-phenylbutanoic acid (3.5 g) is added diethylamine (1.53 mL, 1 eq) and 30% formaldehyde (1.78 mL) at 0° C. The mixture is stirred overnight at a temperature of about 20° C. and is then taken up with diethyl ether (100 mL). The organic phase is separated after settling takes place, washed with 10% aqueous citric acid solution (40 mL) and finally dried over sodium sulphate. After filtering and concentrating to dryness, 2.2 g of ethyl 2-(phenylethyl)acrylate is obtained in a 71% yield in the form of a yellow oil, having the following characteristics: $R_f$=0.86 [methylene chloride/methanol (9:1 by volume)].

The ethyl 2-(phenylethyl)acrylate thereby obtained (2.2 g) is treated overnight with sodium hydroxide (1.5 eq) in an acetone/water (2:1 by volume) mixture at a temperature of about 20° C. The mixture is concentrated to dryness and the residue is then taken up with water (30 mL). The aqueous phase is acidified to pH 2 by adding hydrochloric acid.

The aqueous mixture is then extracted three times with ethyl acetate (20 mL). The organic phase is washed with water (15 mL) and saturated sodium chloride solution (15 mL) and dried over sodium sulphate. After filtering and concentrating to dryness, 1.8 g of 2-(1-phenylethyl)acrylic acid is obtained in a 95% yield in the form of a white solid, having the following characteristics: melting point (m.p.): 115° C.; $R_f$=0.61 [methylene chloride/methanol (9:1 by volume)].

The acid thereby obtained (1.5 g) is heated to 80° C. with thioacetic acid (6 mL). After concentration to dryness, 0.21 g of 2-acetylthiomethyl-3-phenylbutanoic acid is obtained in a 98% yield in the form of a yellow oil, having the following characteristics: $R_f$=0.73 [methylene chloride/methanol (9:1 by volume)].

EXAMPLE 55

2-Acetylthiomethyl-3-phenylbutanoic Acid

Sodium hydride (4.15 g) in 80% suspension in oil is added to a solution of triethyl phosphonoacetate (25 mL) in anhydrous dimethylformamide (36 mL). After 15 minutes at 0° C., 1-bromo-1-phenylethane (18 mL, 1.05 eq) is added. The mixture is stirred overnight at a temperature of about 20° C. under a nitrogen atmosphere. After evaporation of dimethylformamide, the residue is taken up with ethyl acetate (200 mL). The organic phase is washed three times with water (60 mL) and then with saturated sodium chloride solution (60 mL) and finally dried over sodium sulphate. After filtering and concentrating to dryness, 40.3 g. of diethyl 2-(1-phenylethyl)phosphonoacetate is obtained in a 97% yield in the form of an oil, having the following characteristics: $R_f$=0.57 [cyclohexane/ethyl acetate/acetic acid (5:5:0.5 by volume)].

The diethyl 2-(1-phenylethyl)phosphonoacetate (40.3 g) is dissolved in 37% formaldehyde (65 mL), and potassium carbonate (51 g) is then added. The mixture is heated to reflux for 3 hours 30 minutes. After cooling, the mixture is taken up with hexane (400 mL). The organic phase is washed with water twice (100 mL) and then with saturated sodium chloride solution (100 mL) and finally dried over sodium sulphate. After filtering and concentrating to dryness, 24.2 g of ethyl 2-(1-phenylethyl)acrylate is obtained in a 96% yield in the form of an oil, the characteristics of which are identical to those of the title compound obtained in Example 54.

EXAMPLE 56

3-Acetylthio-2-(1-indanyl)propanoic Acid

Using the procedure described in Example 55, but starting with 1-bromoindane and triethyl phosphonoacetate, ethyl 2-(1-indanyl)acrylate is obtained, which compound, by the action of thioacetic acid under the conditions described in Example 54, yields 3-acetylthio-2-(1-indanyl)propanoic acid in the form of a pale yellow oil, having the following characteristics: $R_f$=0.60 [hexane/ethyl acetate/acetic acid (5:5:0.5 by volume)].

EXAMPLE 57

2-Acetylthiomethyl-3-(4-hydroxyphenyl)butanoic Acid

Using the procedure described in Example 54, but starting with 1-bromo-1-(4-hydroxyphenyl)ethane, 2-acetylthiomethyl-3-(4-hydroxyphenyl)butanoic acid is obtained, having the following characteristics: m.p.: 48° C.; $R_f$=0.58 [methylene chloride/methanol (9:1 by volume)].

EXAMPLE 58

2-Acetylthiomethyl-3-[(4-fluoro)phenyl]butanoic Acid

Working as in Example 54, but starting with 1-bromo-1-[(4-fluoro)phenylethane, 2-acetylthiomethyl-3-[(4-fluoro)phenyl]butanoic acid is obtained in a 98% yield as a thick oil having the following characteristics: $R_f$=0.38 [n-hexane/ethyl acetate/acetic acid (7:3:0.5 by volume)].

EXAMPLE 59

2-Acetylthiomethyl-3-[(3,4-difluoro)phenyl]butanoic Acid

Working as in Example 54, but starting with 1-bromo-1-[(3,4-difluoro)phenyl]ethane, 2-acetylthiomethyl-3-[(3,4difluoro)phenyl]butanoic acid is obtained in a 95% yield as a thick oil having the following characteristics: $R_f$=0.33 hexane/ethyl acetate (1:1 by volume)].

Preparation of Compounds of the Development

EXAMPLE 60

N-(2-Acetylthiomethyl-1-oxo-3-phenylbutyl)tyrosine Benzyl Ester

2-Acetylthiomethyl-3-phenylbutanoic acid (5 g) is dissolved in dry tetrahydrofuran (25 mL). A solution of (S)-tyrosine benzyl ester p-tosylate (1 eq) and triethylamine (1 eq) in chloroform (25 mL), a solution of 1-hydroxybenzotriazole (1 eq) in tetrahydrofuran (30 mL) and a solution of dicyclohexylcarbodiimide (1.2 eq) in chloroform (25 mL) are added successively at 0° C. The mixture is stirred for 1 hour at 0° C. and then overnight at a temperature in the region of 20° C. After filtering, the mixture is concentrated to dryness and the residue is then taken up with ethyl acetate (80 mL). The organic phase is washed successively with 10% citric acid solution (20 mL), water (20 mL), saturated sodium bicarbonate solution (20 mL), water (20 mL) and saturated sodium chloride solution (20 mL). After drying over sodium sulphate, filtering and concentrating to dryness, 8 g of N-(2-acetylthiomethyl-1-oxo-3-phenylbutyl)tyrosine benzyl ester is obtained in an 80% yield in the form of a white solid, having the following characteristics: $R_f$=0.65 [chloroform/methanol (9.5:0.5 by volume)].

The product is purified by chromatography on silica.

EXAMPLE 61

N-(2-Mercaptomethyl-1-oxo-3-phenylbutyl)tyrosine 1 g of the material prepared in Example 60 is dissolved in a degassed acetone/water (2:1 by volume) mixture. 1M sodium hydroxide (4 eq) is added at 0° C. and under a nitrogen atmosphere. The mixture is stirred for 5 hours at a temperature of about 20° C. After filtering and acidifying to pH 1, the organic material is extracted three times with degassed chloroform (15 mL). The organic phase is dried over sodium sulphate. After filtering and concentrating to dryness, 0.73 g of N-(2-mercaptomethyl-1-oxo-3-phenylbutyl)tyrosine is obtained in an 81% yield, the characteristics of which are as follows: m.p.: 80° C.; $R_f$=0.43 [methylene chloride/methanol/acetic acid (9:1:0.5 by volume)].

EXAMPLE 62

N-(Acetylthiomethyl-1-oxo-3-phenylbutyl)glycine Benzyl Ester

Using the procedure described in Example 60, starting with 2-acetylthiomethyl-3-phenylbutanoic acid and glycine benzyl ester, and after purifying by chromatography, eluting with a cyclohexane/ethyl acetate (6:4 by volume) mixture, N-(acetylthiomethyl-1-oxo-3-phenylbutyl)glycine benzyl ester is obtained in a 61% yield, the characteristics of which are as follows: $R_f$=0.39 [cyclohexane/ethyl acetate (6:4 by volume)].

EXAMPLE 63

N-(2-Mercaptomethyl-1-oxo-3-phenylbutyl)glycine

Using the procedure described in Example 60, starting with the material prepared in Example 62, N-(2-mercaptomethyl-1-oxo-3-phenylbutyl)glycine is obtained in an 89% yield, the characteristics of which are as follows: m.p.: 129° C.; $R_f$=0.62 [methylene chloride/methanol/acetic acid (9:1:0.5 by volume)].

EXAMPLE 64

N-(2-Acetylthiomethyl-1-oxo-3-phenylbutyl)-O-benzylserine Benzyl Ester

Using the procedure described in Example 60, starting with 2-acetylthiomethyl-3-phenylbutanoic acid and O-benzylserine benzyl ester, and after purification by chromatography, eluting with a hexane/ethyl acetate (8:2 by volume) mixture, N-(2-acetylthiomethyl-1-oxo-3-phenylbutyl)-O-benzylserine benzyl ester is obtained in a 62% yield, the characteristics of which are as follows: $R_f$=0.16 [hexane/ethyl acetate (8:2 by volume)].

EXAMPLE 65

N-(2-Mercaptomethyl-1-oxo-3-phenylbutyl)-O-benzylserine

Using the procedure described in Example 61, starting with the material prepared in Example 64, N-(mercaptomethyl-1-oxo-3-phenylbutyl)-O-benzylserine is obtained in a 72% yield in the form of an oil, having the following characteristics: $R_f$=0.29 [methylene chloride/methanol (9:1 by volume)].

EXAMPLE 66

N-(2-Acetylthiomethyl-1-oxo-3-phenylbutyl)alanine Benzyl Ester

Using the procedure described in Example 60, starting with 2-acetylthiomethyl-3-phenylbutanoic acid and alanine benzyl ester, and after purification by chromatography, eluting with a cyclohexane/ethyl acetate (75:25 by volume) mixture, N-(2-acetylthiomethyl-1-oxo-3-phenylbutyl)alanine benzyl ester is obtained in a 68% yield, the characteristics of which are as follows: $R_f$=0.31 [hexane/ethyl acetate (75:25 by volume)].

EXAMPLE 67

N-(2-Mercaptomethyl-1-oxo-3-phenylbutyl)alanine

Using the procedure described in Example 61, starting with the material prepared in Example 66, N-(2-mercaptomethyl-1-oxo-3-phenylbutyl)alanine is obtained in a 75% yield in the form of a colorless oil, having the following characteristics: $R_f$=0.27 [methylene chloride/methanol (9:1 by volume)].

EXAMPLE 68

N-(2-Acetylthiomethyl-1-oxo-3-phenylbutyl)norleucine Benzyl Ester

Using the procedure described in Example 60, but starting with 2-acetylthiomethyl-3-phenylbutanoic acid and norleucine benzyl ester, and after purifying by chromatography, eluting with a hexane/ethyl acetate (75:25 by volume) mixture, N-(2-acetylthiomethyl-1-oxo-3-phenylbutyl)norleucine benzyl ester is obtained in a 75% yield in the form of an oil, having the following characteristics: $R_f$=0.46 [hexane/ethyl acetate(6.5:3.5 by volume)].

EXAMPLE 69

N-(2-Mercaptomethyl-1-oxo-3-phenylbutyl)norleucine

Using the procedure described in Example 61, but starting with the material prepared in Example 68, N-(2-mercaptomethyl-1-oxo-3-phenylbutyl)norleucine is obtained in a 90%

EXAMPLE 70

N-[3-Acetylthio-2-(1-indanyl)-1-oxopropyl]alanine Benzyl Ester

Using the procedure described in Example 60, but starting with 3-acetylthio-2-(1-indanyl)propanoic acid and alanine benzyl ester, N-[3-acetylthio-2-(1-indanyl)-1-oxopropyl)alanine benzyl ester is obtained in a 72% yield in the form of a white solid, having the following characteristics: m.p.: 95° C.; $R_f$=0.17 [cyclohexane/ethyl acetate (4:1 by volume)].

EXAMPLE 71

N-[3-Mercapto-2-(1-indanyl)-1-oxopropyl]alanine

Using the procedure described in Example 61, but starting with the material prepared in Example 70, N-[3-mercapto-2-(1-indanyl)-1-oxopropyl]alanine is obtained in a 96% yield, the characteristics of which are as follows: m.p.: 121° C.; $R_f$=0.22 [methylene chloride/methanol (9:1 by volume)].

EXAMPLE 72

N-[2-Acetylthiomethyl-3-(4-hydroxyphenyl)-1-oxobutyl]alanine Benzyl Ester

Using the procedure described in Example 60, but starting with 2-acetylthiomethyl-3-(4-hydroxyphenyl)butanoic acid and alanine benzyl ester, N-[2-acetylthiomethyl-3-(4-hydroxyphenyl)-1-oxobutyl]alanine benzyl ester is obtained in a 69% yield, the characteristics of which are as follows: $R_f$=0.22 [hexane/ethyl acetate (65:35 by volume)].

EXAMPLE 73

N-[2-Mercaptomethyl,3-(4-hydroxyphenyl)-1-oxobutyl]alanine

Using the procedure described in Example 61, but starting with the material prepared in Example 72, N-[2-mercaptomethyl-3-(4-hydroxyphenyl)-1-oxobutyl]alanine is obtained in an 85% yield in the form of a white solid, having the following characteristics: m.p.: 72° C.; $R_f$=0.18 [methylene chloride/methanol (9:1 by volume)].

EXAMPLE 74

N-[2-Acetylthiomethyl-3-(4-hydroxyphenyl)-1-oxobutyl]tyrosine Benzyl Ester

Using the procedure described in Example 60, but starting with 2-acetylthiomethyl-3-(4-hydroxyphenyl)butanoic acid and tyrosine benzyl ester, N-[2-acetylthiomethyl-3-(4-hydroxyphenyl)-1-oxobutyl]tyrosine benzyl ester is obtained in a 78% yield in the form of a white solid, having the following characteristics: $R_f$=0.16 [hexane/ethyl acetate (65:35 by volume)].

EXAMPLE 75

N-[2-Mercaptomethyl-3-(4-hydroxyphenyl)-1-oxobutyl]tyrosine

Using the procedure described in Example 61, but starting with the material prepared in Example 74, N-[2-mercaptomethyl-3-(4-hydroxyphenyl)-1-oxobutyl]tyrosine is obtained in a 70% yield in the form of a white solid, having the following characteristics: m.p.: 115° C.; $R_f$=0.27 [methylene chloride/methanol (8:2 by volume)].

EXAMPLE 76

N-[2-Adamantoylthiomethyl-1-oxo-3-phenylbutyl]alanine

The material prepared in Example 67 (1.7 g) is dissolved in degassed water (18 mL). To the solution under a nitrogen atmosphere and at 0° C. is added a $1.3 \times 10^{-2}$M solution of sodium hydroxide (2.2 eq) and adamantoyl chloride (1.33 g, 1.1 eq). The mixture is stirred for four hours at ambient temperature. The mixture is then acidified to pH 3 with 1M hydrochloric acid and extracted with ethyl acetate. The organic phase is washed with water and then a saturated NaCl solution. The organic phase is dried over anhydrous $Na_2SO_4$, filtered and evaporated to dryness. A white solid (2 g) is obtained in a yield of 74% having the following characteristics: m.p.: 80° C.; $R_f$=0.45 [chloroform/methanol/acetic acid (7:3:0.3 by volume)].

EXAMPLE 77

N-[2-Acetylthiomethyl-3-(4-fluorophenyl)-1-oxobutyl]alanine Benzyl Ester

Working as in Example 60, but starting with 2-acetylthiomethyl-3-(4-fluorophenyl)butanoic acid and benzyl esters of alanine, the title compound is obtained in a yield of 73% as an oil having the characteristics:

$R_f$=0.23 [cyclohexane/ethyl acetate (7:3 by volume)].

EXAMPLE 78

N-[2-Acetylthiomethyl-3-(4-fluorophenyl)-1-oxobutyl]alanine

Working as in Example 61, but starting with the material prepared in Example 77, the title compound is obtained in a yield of 78% as a white solid having the following characteristics: m.p.: 93° C., $R_f$=0.5 [methylene chloride/methanol/acetic acid (9:1:0.5 by volume)].

EXAMPLE 79

N-[2-Acetylthio-3-(4-fluorophenyl)-1-oxobutyl]tyrosine Benzyl Ester

Working as in Example 60, but starting with 2-acetylthio-3-(4-fluorophenyl)butanoic acid and benzyl ester of lysine, the title compound is obtained in a yield of 89% as a pale yellow oil having the following characteristics: $R_f$=0.14 [cyclohexane/ethyl acetate (2:3 by volume)].

EXAMPLE 80

N-[2-Acetylthio-3-(4-fluorophenyl)-1-oxobutyl]tyrosine

Working as in Example 61, but starting with the material prepared in Example 79, the title compound is obtained in a yield as an oily composition having the following characteristics: $R_f$=0.45 [methylene chloride/methanol/acetic acid (9:1:0.5 by volume)].

EXAMPLE 81

N-[2-Acetylthiomethyl-3-(3,4-difluorophenyl)-1-oxobutyl]alanine Benzyl Ester Working as in Example 60, but starting with 2-acetylthiomethyl-3-(3,4-difluoro)phenylbutanoic acid and benzyl ester of alanine, the title compound is formed as an oil having the following characteristics: $R_f=0.2$ [hexane/ethyl acetate (3:1 by volume)].

EXAMPLE 82

N-[2-Mercaptomethyl-3-(3,4-difluorophenyl)-1-oxobutyl]alanine

Working as in Example 61, but using the material prepared in Example 81, the title compound is obtained in a yield of 72% as a white solid having the following characteristics: m.p.: 61° C.; $R_f=0.17$ [methylene chloride/methanol (9:1 by volume)].

EXAMPLE 83

N-[2-Mercaptomethyl-3-(3,4-difluorophenyl)-1-oxobutyl]tyrosine Benzyl Ester

Working as in Example 60, but using the benzyl ester of tyrosine and 2-acetylthiomethyl-3-(3,4-difluoro)phenylbutanoic acid, the title compound is obtained in a yield of 80% as an oil having the following characteristics: $R_f=0.26$ [cyclohexane/ethyl acetate (6:4 by volume)].

EXAMPLE 84

N-[2-Mercaptomethyl-3-(3,4-difluorophenyl)-1-oxobutyl]tyrosine

Working as in Example 61, but using the material prepared in Example 83, the title compound is obtained in a yield of 80% as a pale yellow oil having the following characteristics: $R_f=0.10$ [methylene chloride/methanol (9:1 by volume)].

EXAMPLE 85

Resolution of 2-Acetylthiomethyl-3-phenylbutanoic (ATBA) Acid to Four Diastereomers (I–IV)

(A) Resolution Using (R)-(+)-1-(1-Naphthyl)ethylamine to Yield ATBA-I

2-Acetylthiomethyl-3-phenylbutanoic acid (5 g) is dissolved in ethanol (50 mL) and (R)-(+)-1-(1-naphthyl)ethylamine (3.4 g) is added to the ethanol solution. Ethyl ether (50 mL) is then added. The mixture is cooled in an ice bath and after scratching the reaction vessel, a white precipitate is formed. The solution is stored at about 0° C. for about 18 hours. The precipitate is filtered and washed with ethyl ether.

1.47 g of a white precipitate is obtained. The precipitate is recrystallized from absolute ethanol to yield 0.42 g of off-white crystals of a diastereomer, (R)-(+)-1-(1naphthyl)ethylammonium 2-acetylthiomethyl-3-phenylbutanoate salt (ATBA-I salt).

The free acid ATBA-I is regenerated by contacting the ATBA-I salt (50 mg) with aqueous acid (10% hydrochloric) and extracting with methylene chloride. The methylene chloride is evaporated and 32.1 mg of ATBA-I is obtained as an oil having the following characteristics: $[\alpha]_D^{RT}=+78.25$ [28.5 mg in methanol (1 mL)].

(B) Resolution Using (S)-(–)-1-(1-Naphthyl)ethylamine to Yield ATBA-II

The procedure in Example 85(A) above is used, except that (S)-(–)-1-(1-naphthyl)ethylamine is used as the amine. 1.2 g of a white precipitate (ATBA-II salt) is obtained and following recrystallization 0.31 g is obtained.

The free acid (ATBA-II) is regenerated from the salt (50 mg) in a yield of 28.7 mg as an oil having the following characteristics: $[\alpha]_D^{RT}=-79.38$ [29.1 mg in methanol (1 mL)].

(C) Resolution Using (S)-Methylbenzylamine to Yield ATBA-III

2-Acetylthiomethyl-3-methylbutanoic acid (5 g) is dissolved in ethanol (35 mL) and a solution of (S)-methylbenzylamine (2.4 g) in methanol (10 mL) is added. The mixture is diluted to 200 mL with ethyl ether. A precipitate forms and the solution is cooled at about 0° C. for about 18 hours.

The colorless crystalline solid is filtered, washed with ethyl ether and dried to yield 2 g of ATBA-III salt. The solid is recrystallized twice from a mixture of ethyl acetate/ethanol (2:1) (25 mL) to yield 1 g of ATBA-III salt.

The free acid ATBA-III is regenerated by contacting the ATBA-III salt with aqueous acid (10% hydrochloric acid) and extracting with methylene chloride. The methylene chloride is evaporated and 0.67 g of ATBA-III is obtained as a colorless crystalline solid.

(D) Resolution Using (R)-Methylbenzylamine to Yield ATBA-IV

The procedure in Example 85(C) above is used except that (R)-methylbenzylamine is used to obtain 1.1 g of ATBA-IV as a colorless crystalline solid.

EXAMPLE 86

Preparation of Four Diastereomers of N-(2-Acetylthiomethyl-1-oxo-3-phenylbutyl)tyrosine Benzyl Ester (ATBAT-(I–IV)) by Synthetic Coupling of Resolved Reactants (A) N-(2-Acetylthiomethyl-1-oxo-3-phenylbutyl)tyrosine Benzyl Ester (ATBAT-IV)

ATBA-IV (0.2 g) (prepared in Example 85(B)) is dissolved in methylene chloride (5 mL). (S)-Tyrosine benzyl ester p-tosylate (0.35 g), 1-(3-dimethylaminopropyl)-3-ethylcarbodiimide (0.15 g), hydroxybenzotriazole (0.11 g) and N-methylmorpholine (0.19 g) are added to the solution and the mixture is stirred at 20° C. for 18 hours.

The solvent is removed in vacuo and the residue is contacted with aqueous acid (10% hydrochloric acid) and extracted with ethyl acetate. The organic phase is separated and washed consecutively with water (20 mL), saturated sodium bicarbonate solution (20 mL) and water (20 mL). The organic phase is dried and evaporated to yield a light yellow gum. The gum is chromatographed on silica gel using a mixture of hexane/ethyl acetate (1:1) to yield a colorless gum (ATBAT-IV) (0.26 g; 65%) having the following characteristic: $[\alpha]_D^{25}=+98.90$.

(B) N-(2-Acetylthiomethyl-1-oxo-3-phenylbutyl)tyrosine Benzyl Ester (ATBAT-III)

Using the procedure of Example 86(A), except starting with ATBA-III (prepared in Example 85(A)), ATBAT-III is obtained after crystallization having the characteristics: m.p.: 151°–153° C.; $[\alpha]_D^{25}=-89.7$.

(C) N-(2-Acetylthiomethyl-1-oxo-3-phenylbutyl)tyrosine Benzyl Ester (ATBAT-II)

Using the procedure of Example 86(A), except starting with ATBA-II (prepared in Example 85(B)), ATBAT-II is obtained.

(D) N-(2-Acetylthiomethyl-1-oxo-3-phenylbutyl)tyrosine Benzyl Ester (ATBAT-I)

Using the procedure of Example 86(A), except starting with ATBA-I (prepared in Example 85(A)), ATBAT-I is obtained after crystallization having the characteristics: m.p.: 135°–137° C.

EXAMPLE 87

Preparation of Diastereomers of N-(2-Acetylthiomethyl-1-oxo-3-phenylbutyl)tyrosine Benzyl Ester (ATBAT-(I–IV)) by Column Chromatography The diastereomers of N-(2-acetylthiomethyl-1-oxo-3-phenylbutyl)tyrosine benzyl ester are also obtained by column chromatography using Hewlett-Packard ODS Hypersil column (5µ, 200×4.6 mm i.d.). The material prepared in Example 60 is dissolved in methanol and placed on the column. A mobile phase of methanol/water (62:38 by volume) with 0.2% trifluoroacetic acid is employed in effecting the separation. The flow rate is 1.0 mL/min. The material prepared is detected at UV of 215 nm. The retention times of the four diastereomers are 22.7, 24.75, 28.5 and 30 minutes, respectively.

EXAMPLE 88

Two Diastereomers of N-(2-Mercaptothiomethyl-1-oxo-3-phenylbutyl)tyrosine (MTBT-(I–II))

(A) N-(2-Mercaptothiomethyl-1-oxo-3-phenylbutyl)tyrosine (MTBT-I)

Lithium hydroxide hydrate (1.8 mg) is dissolved in solvent comprising tetrahydrofuran/methanol/water (1:1:1 by volume). The solvent is purged with nitrogen gas. ATBAT-IV (21 mg) (prepared in Example 86(A)) is added to the solution and stirred for 75 minutes at 20° C. The solution is then diluted with water (5 mL), washed twice with chloroform (3 mL), acidified with 10% hydrochloric acid (2 mL) and extracted five times with chloroform (4 mL). The combined organic phases are dried over magnesium sulphate and evaporated to leave 16 mg of a colorless gum (MTBT-I) having >95% purity.

(B) N-(2-mercaptothiomethyl-1-oxo-3-phenylbutyl)tyrosine (MTBT-II)

Using the procedure of Example 87(A), except starting with ATBAT-II (prepared in Example 86(B)), MTBT-II (9.7 mg) is obtained after crystallization having >98% purity.

Table IV below presents selected pharmacological data for the N-mercaptoacyl(amino acid or peptide) compounds having both ACE and NEP inhibitory properties. Pharmacological activity of N-(2-mercapto-methyl-3-phenyl-1-oxopropyl)glycine (thiorphan) is also provided, which is very closely related in structure to the compounds of the present development, for comparison to show that thiorphan manifests activity only against NEP.

TABLE IV

Inhibitory effect on neutral endopeptidase (NEP) and peptidyldipeptidase A (ACE)

| EXAMPLE | IC$_{50}$ (nM) NEP | IC$_{50}$ (nM) ACE |
|---|---|---|
| 61 | 2.5 | 1.8 |
| 63 | 1.3 | 25 |
| 65 | 4 | 71 |
| 67 | 2 | 2.8 |
| 69 | 3.1 | 5.8 |
| 71 | 1.3 | 7.9 |
| 73 | 3.5 | 6.2 |
| 75 | 1.8 | 3.5 |
| 78 | 1.9 | 8.5 |
| 80 | 4.8 | 5.9 |
| 82 | 3 | 5 |
| 84 | 6.3 | 3.5 |
| 88(A) | 1 | 3 |
| 88(B) | 3.1 | 52 |
| Thiorphan | 2.0 | 140 |

Methods for the Preparation of Compounds Which Are the Subject Also of International Application No. 3

Throughout the discussion which follows and which is directed to methods for the preparation of compounds that are the subject also of international application No. 3, $R_1$, $R_2$, $R_4$, $R_5$, $R_6$, $R_7$ and R' are as described previously in connection with the discussion involving international application No. 3.

S-lipophilic aliphatic carbonyl [N-mercaptoacyl(amino acid or peptide)]compounds may be prepared by acylating the appropriate N-mercaptoacyl(amino acid or peptide) with the appropriate lipophilic aliphatic carbonyl halide. The reaction may be carried out in the absence or presence of a base, such as aqueous sodium hydroxide and pyridine, and may be carried out under an inert atmosphere, such as nitrogen. It is also preferred that the reaction medium is degassed to prevent the mercapto compound from forming a disulfide linked dimer. See "Preparative Organic Chemistry", edited by G. Hilgetag and A. Martini, at page 642, J. Wiley & Sons (1972).

N-(mercaptoacyl)amino acids may be prepared by hydrolyzing the compound formed by acylation of an amino acid of formula (VIII) above by means of an acid of formula (IX$_{LA}$)

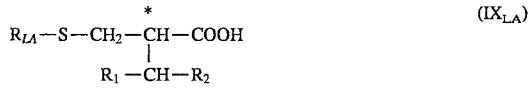

wherein $R_{LA}$ is a lower acyl group, under the customary conditions used in peptide chemistry, described, for example, by Bodansky et al., "Peptide Synthesis", J. Wiley & Sons Edit. The acylation and hydrolysis are preferably carried out under the conditions described above in connection with the preparation of the compound of formula (IV).

The compounds of general formula (IX$_{LA}$) may be obtained by the Michael addition of a sulphur derivative of formula (X$_{LA}$)

wherein $R_{LA}$ is as described above, to an acrylic acid of formula (XI) above.

Preferably, thioacetic acid or thiobenzoic acid is used as a sulphur derivative of formula (XL$_{LA}$).

The acrylic acid of formula (XI) may be obtained by using synthetic methodology as described hereinbefore in connection with subject matter which is described also in international application No. 2.

N-(mercaptoacyl)peptides may be prepared by hydrolyzing the compound formed by the acylation of a dipeptide of the formula (VI) by an acid of formula (VII$_{LA}$)

wherein R$_{LA}$ is as described above and under conditions described hereinbefore. The hydrolysis is preferably carried out in an alkaline medium, working in an inert medium so as to avoid oxidation of the mercapto group.

The acid reactant may be prepared from the corresponding α-amino acid by halogenating deamination according to Fischer, Ann., 357, 1–24 (1907), followed by nucleophilic substitution of the halogen atom.

Lipophilic aliphatic carbonyl halides may be prepared from the following lipophilic aliphatic carboxylic compounds when they are in the acid or anhydride forms: camphorcarboxylic acid, camphanecarboxylic acid, 3-methyl adamantyl carboxylic acid, noradamantyl carboxylic acid, norbornane carboxylic acid, 3-methyl-3-bromo-1-adamantyl carboxylic acid, methyl 1-methoxybicyclo[2.2.2.]-oct-5-ene-2-carboxylate, mono methyl cis-5-norbornene-endo-2,3-dicarboxylate, methyl-5-norbornene-2,3-dicarboxylic anhydride, (1R)-(–)-myrtentoic acid, cis-5-norbornene-endo-2,3-dicarboxylic acid, 5-norbornen-2-yl acetate, 2-norbornaneacetic acid, anti-3-oxo-tricyclo[2.2.1.0$^{2,6}$]-heptane-7-carboxylic acid, 2-decalincarboxylic acid and 2-quinuclidinecarboxylic acid. See "Preparative Organic Chemistry" edited by G. Hilgetag and A. Martini at pages 242–251, J. Wiley & Sons (1972).

Resolved forms of the compounds according to the present development may be prepared by standard practices known to those skilled in the art, such as fractional crystallization and column chromatography. For example, compounds of formula (IX$_{LA}$), for example, an acylthioalkanoic acid, may be resolved by fractional recrystallization with optically active bases, such as methylbenzylamine and 1-(1-naphthyl)ethylamine, and then resolved compounds of formula (IX$_{LA}$) may be reacted with an optically active amino acid according to the acylation reaction described above to yield a resolved N-(mercaptoacyl)amino acid.

Embodiments of the present development are described in the following non-limiting examples which include pharmacological test procedures believed to correlate to therapeutic activity in humans and other animals.

EXAMPLE 89

N-[2-Adamantoylthiomethyl-1-oxo-3-phenylbutyl]alanine

The material prepared in Example 67 (1.7 g) is dissolved in degassed water (18 ml). To the solution under a nitrogen atmosphere and at 0° C. is added a solution of 1.3×10$^{-2}$M sodium hydroxide (2.2 eq) and adamantoyl chloride (1.33 g, 1.1 eq). The mixture is stirred for four hours at ambient temperature. The mixture is then acidified to pH 3 with 1M hydrochloric acid and extracted with ethyl acetate. The organic phase is washed with water and then a saturated NaCl solution. The organic phase is dried over anhydrous Na$_2$SO$_4$, filtered and evaporated to dryness. A white solid (2 g) is obtained in a yield of 74% having the following characteristics: m.p. 80° C.; R$_f$=0.45 [chloroform/methanol/acetic acid (7:3:0.3 by volume)].

EXAMPLE 90

(S,S,S)-N-[2-Adamantoylthiomethyl-1-oxo-3-phenylbutyl]alanine

The title compound is prepared as in Example 89, except starting with the material prepared in Example 88(A).

EXAMPLE 91

Comparison of In vivo inhibition of NEP in mouse by orally administered
[S,S,S]—N-[2-adamantoylthiomethyl-1-oxo-3-phenylbutyl]alanine (91A) and diastereomeric mixture of
N-[2-acetylthiomethyl-1-oxo-3-phenylbutyl]alanine (91B)

[S,S,S]-N-[2-Adamantoylthiomethyl-1-oxo-3-phenylbutyl]alanine, a diastereomeric mixture of N-[2-acetylthiomethyl-1-oxo-3-phenylbutyl]alanine (four diastereomers) and a control solution of saline are orally administered at a concentration of 2.6×10$^{-5}$ mole/kg) in mice at t=o. At 30 and 480 minutes following their administration, a highly selective and tritiated, NEP inhibitor, [$^3$H]HACBOGly (1 μCi) (Waksman et al., Proc. Natl. Acad. Sci. USA, 1523–1527 (1986) is administered by i.v. route to a mouse. The mouse is killed 15 minutes thereafter, and the kidney is rapidly set apart and homogenized at 4° C. in a Tris HCl buffer 50 mM (pH 7.4). The homogenate is filtered and the radioactivity bound to the filter is measured by liquid scintillation. The non-specific binding is determined after co-injection of [$^3$H]HACBOGly with 10,000 equivalents of the specific NEP inhibitor, retrothiorphan (Roques et al., Proc. Natl. Acad. Sci. USA, 80 3178–3182 (1983).

The inhibition of NEP in the kidney is expressed as the difference (in %) between specific [$^3$H]HACBOGly binding in the absence of inhibitor (controls injected with saline) and in the presence of inhibitor. The inhibition values in Table V are the mean value of three determinations.

TABLE V

| | % Inhibition | | | |
| --- | --- | --- | --- | --- |
| | ACE | | NEP | |
| Time (min.) | 91(A) | 91(B) | 91(A) | 91(B) |
| 30 | 75 | 30 | 85 | 65 |
| 240 | 30 | 15 | 70 | 45 |

EXAMPLE 92

Comparison of in vivo inhibition of ACE in mouse by orally administered
(S,S,S)-N-[2-adamantoylthiomethyl-1-oxo-3-phenylbutyl]alanine (92(A)) and
diastereomeric mixture of
N-[2-acetylthiomethyl-1-oxo-3-phenylbutyl]alanine (92(B))

The protocol in Example 91 is used also to determine NEP inhibition except for the following: the selective tritiated ACE inhibitor is [$^3$H]Trandaloprilate (0.5 μCi); and the non-specific binding is determined by the co-administration of [$^3$H]Trandaloprilate with 1000 eq. of captopril. The NEP inhibition values are given in Table V above.

Under the same reaction parameters as in Example 92, ACE inhibition is determined at 30, 60, 120 and 240 minutes for N-(2-acetylthiomethyl-1-oxo-3-phenylbutyl)alanine as a mixture of four stereoisomers (-□-), N-(2-adamantylthiomethyl-1-oxo-3-phenylbutyl)alanine as a mixture of four stereoisomers (—O—) and the single stereoisomer (S,S,S)-N-(2-adamantylthiomethyl-1-oxo-3-phenylbutyl)alanine (-■-). FIG. 1 graphically represents the results and shows the ACE inhibitory activity of various compounds of the invention.

We claim:

1. An S-lipophilic aliphatic carbonyl [N-mercaptoacyl(amino acid or peptide)] compound.

2. A process for preparing the compound according to claim 1 comprising acylating an N-mercaptoacyl(amino acid or peptide) with a lipophilic aliphatic carbonyl halide.

3. a pharmaceutical composition comprising a compound according to claim 1 and a pharmaceutically acceptable carrier.

4. A compound of the formula $$R-S-X \quad (I)$$

wherein:

X is a residue of the formula $$-Y-\overset{*}{C}H-CONH-\overset{*}{C}H-Z-COOR'; \quad (II)$$
$$\underset{R_1-CH-R_2}{|} \quad \underset{R_3}{|}$$

Y is a chemical bond or $-CH_2-$;

Z is a chemical single bond or $$-CON-\overset{R_6}{\underset{|}{C}}H-;$$
$$\phantom{-CON-}*$$

R is hydrogen, acyl, aroyl, cycloalkylcarbonyl, lipophilic aliphatic carbonyl or $-S-X$;

$R_1$ is hydrogen or alkyl;

$R_2$ is hydrogen, alkyl, aryl, heteroaryl, aralkyl, alkoxy, alkoxy-lower alkyl, or aralkyloxy;

$R_1$ and $R_2$ are also linked together to form aryl;

when $R_2$ is aryl, heteroaryl, aralkyl or aralkyloxy, $R_1$ is also alkylene which is linked to $R_2$ to form fused aromatic cycloalkyl;

$R_3$ is hydrogen, alkyl, aryl, alkoxy, aryloxy or $-CH(R_4)(R_5)$, where $R_4$ has the same definition as $R_1$ and $R_5$ has the same definition as $R_2$;

$R_6$ is hydrogen or alkyl;

$R_7$ is cycloalkyl, aralkyl, aryloxy-lower alkyl or alkoxy-lower alkyl;

$R_6$ and $R_7$ are also linked together to form, together with the nitrogen and carbon atoms to which $R_6$ and $R_7$ are respectively attached, heterocyclyl;

R' is hydrogen, alkyl, aralkyl, acyl, aroyl or lipophilic aliphatic carbonyl, with the proviso that when $R_1$ is hydrogen or methyl, $R_3$ is $-CH(R_4)(R_5)$ wherein one of $R_4$ and $R_5$ is hydrogen, methyl, n-propyl or i-propyl and the other of $R_4$ and $R_5$ is hydrogen or methyl and Z is $-CON(R_6)-CH(R_7)-$ wherein $R_6$ and $R_7$ are linked together to form, together with the nitrogen and carbon atoms to which $R_6$ and $R_7$ are respectively attached, prolinyl, hydroxyprolinyl, methoxyprolinyl or thiazolidinyl, then $R_2$ is not hydrogen, alkyl of 1 to 5 carbon atoms, unsubstituted phenyl or unsubstituted benzyl;

or a pharmaceutically acceptable salt thereof.

5. The compound according to claim 4 wherein:

Y is $-CH_2-$;

Z is a chemical single bond;

R is hydrogen, acyl, aroyl, cycloalkylcarbonyl or $-S-X$;

$R_1$ is alkyl;

$R_2$ is aryl or heteroaryl;

$R_1$ is also alkylene which is linked to a carbon atom of $R_2$ that is at a position which is ortho to the point of attachment of $R_2$ to the methine (CH) group;

$R_3$ is hydrogen, alkyl, aryl, heteroaryl, alkoxy or aryloxy; and

R' is hydrogen, alkyl, aralkyl, acyl or aroyl.

6. The compound according to claim 5 wherein:

R is hydrogen, acyl, benzoyl in which the phenyl ring is unsubstituted or substituted with halogen, hydroxy, alkoxy, amino, dialkylamino or trifluoromethyl, adamantoyl, palmitoyl, pamoyl or $-S-X$;

$R_1$ is methyl or trifluoromethyl;

$R_2$ is phenyl or heteroaryl which is 2-, 3- or 4-pyridyl, N-methyl-2- or -3-pyrrolyl, wherein (A) said phenyl or heteroaryl is unsubstituted or substituted with one or more substituents at a position other than the position which is ortho to the point of attachment of $R_2$ to the methine (CH) group, said substituents being independently halo, hydroxy, acyloxy, alkoxy, phenoxy, phenylthio, amino, dialkylamino, methylenedioxy or ethylenedioxy, or (B) said phenyl or heteroaryl is connected to $R_1$ which is alkylene and which is linked to a carbon atom of $R_2$ at a position that is ortho to the point of attachment of $R_2$ to the methine (CH) group, said alkylene being unsubstituted or substituted with methyl, and wherein said alkylene may contain also, in the alkylene chain, one or more $-W-CH_2-$ or $-CH_2-W-$ diradicals, wherein W is $-N(CH_3)-$;

R3 is hydrogen, trifluoromethyl, alkyl which is substituted or unsubstituted, alkoxy, phenoxy or aryl, said alkyl substituents being independently phenyl, hydroxy, alkoxy, phenoxy, alkylthio, phenylthio, benzyloxy or benzylthio, and wherein phenyl and aryl, and the phenyl portions of phenoxy, phenylthio, benzyloxy and benzylthio, are unsubstituted or substituted with one or more of halo, hydroxy, alkoxy, amino, dialkylamino, methylenedioxy or ethylenedioxy; and R' is hydrogen, methyl, ethyl, benzyl, cyclohexylmethyl, palmitoyl or pamoyl.

7. The compound according to claim 5 which is selected from the group consisting of:

N-(2-acetylthiomethyl-1-oxo-3-phenylbutyl)tyrosine;

N-(2-acetylthiomethyl-1-oxo-3-phenylbutyl)glycine;

N-(2-acetylthiomethyl-1-oxo-3-phenylbutyl)-O-benzylserine;

N-(2-acetylthiomethyl-1-oxo-3-phenylbutyl)alanine;

N-(2-acetylthiomethyl-1-oxo-3-phenylbutyl)norleucine;

N-[3-acetylthio-2-(1-indanyl)-1-oxopropyl]alanine;

N-[2-acetylthiomethyl-3-(4-hydroxyphenyl)-1-oxobutyl]alanine; and

N-[2-acetylthiomethyl-3-(4-hydroxyphenyl)-1-oxobutyl]tyrosine.

8. The compound according to claim 5 which is selected from the group consisting of:

N-(2-mercaptomethyl-1-oxo-3-phenylbutyl)tyrosine;

N-(2-mercaptomethyl-1-oxo-3-phenylbutyl)glycine,

N-(2-mercaptomethyl-1-oxo-3-phenylbutyl)-O-benzylserine,

N-(2-mercaptomethyl-1-oxo-3-phenylbutyl)alanine;

N-(2-mercaptomethyl-1-oxo-3-phenylbutyl)norleucine;

N-[3-mercapto-2-(1-indanyl)-1-oxopropyl]alanine;

N-[2-mercaptomethyl-3-(4-hydroxyphenyl)-1-oxobutyl]alanine; and

N-[2-(1-mercaptomethyl-3-(4-hydroxyphenyl)-1-oxobutyl]tyrosine.

9. The compound according to claim 8 which is N-[(2S,3R)-2-mercaptomethyl-1-oxo-3-phenyl-butyl]-(L)alanine.

10. The compound according to claim 5 wherein the stereochemical configuration of the carbon atoms which are designated with asterisks is selected from the group consisting of R,R,S, S,R,S, S,S,S and R,S,S.

11. The compound according to claim 10 wherein said configuration is selected from the group consisting of S,S,S and R,S,S.

12. A process for the preparation of the compound according to claim 5 comprising acylating an amino acid of the formula

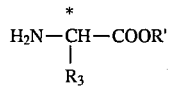     (VIII)

with an acid of the formula

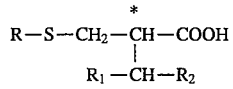     (IX)

13. A pharmaceutical composition comprising a compound according to claim 5 in combination with a pharmaceutically acceptable carrier.

14. A method of treating hypertension in a mammal comprising administering an effective antihypertensive amount of a compound according to claim 5.

* * * * *